(12) United States Patent
Steinmetzer et al.

(10) Patent No.: US 8,569,313 B2
(45) Date of Patent: Oct. 29, 2013

(54) META-SUBSTITUTED PHENYL SULFONYL AMIDES OF SECONDARY AMINO ACID AMIDES, THE PRODUCTION THEREOF, AND USE THEREOF AS MATRIPTASE INHIBITORS

(75) Inventors: Torsten Steinmetzer, Jena (DE); Andrea Schweinitz, Jena (DE); Daniel Donnecke, Victoria (CA)

(73) Assignee: The Medicines Company (Leipzig) GmbH, Leipzig (DE)

( * ) Notice: Subject to any disclaimer, the term of this patent is extended or adjusted under 35 U.S.C. 154(b) by 713 days.

(21) Appl. No.: 12/529,767

(22) PCT Filed: Mar. 5, 2008

(86) PCT No.: PCT/EP2008/001750
§ 371 (c)(1),
(2), (4) Date: Apr. 5, 2010

(87) PCT Pub. No.: WO2008/107176
PCT Pub. Date: Sep. 12, 2008

(65) Prior Publication Data
US 2010/0305090 A1    Dec. 2, 2010

(30) Foreign Application Priority Data

Mar. 6, 2007    (DE) .................. 10 2007 010 815

(51) Int. Cl.
*A01N 43/54* (2006.01)
*A01N 43/40* (2006.01)
*A01N 43/90* (2006.01)
*A61K 31/517* (2006.01)
*A61K 31/519* (2006.01)
*A61K 31/445* (2006.01)

(52) U.S. Cl.
USPC ........ 514/258.1; 514/315; 544/253; 546/184; 546/191

(58) Field of Classification Search
USPC ........ 514/258.1, 315; 544/253; 546/184, 187, 546/191
See application file for complete search history.

(56) References Cited

FOREIGN PATENT DOCUMENTS

WO    2004/101507    11/2004

OTHER PUBLICATIONS

Steinmetzer, et al., Secondary amides of sulfonylated 3-amidinophenylalanine. New potent and selective inhibitors of matriptase, J. of Med. Chem. 49(14), 4116-4126 (2006).*
Streinmetzer, et al., Secondary amides of sulfonylated 3-amidinophenylalanine. New potent and selective inhibitors of matriptase, J. of Med. Chem. 49(14), 4116-4126 (2006).*
International Search Report issuing in PCT/EP2008/001750 on Jul. 30, 2008.

* cited by examiner

*Primary Examiner* — Erich A Leeser
(74) *Attorney, Agent, or Firm* — Roylance, Abrams, Berdo & Goodman, LLP

(57) ABSTRACT

The invention relates to meta-substituted phenyl sulfonyl amides of secondary amino acid amides according to the general formula (I), (II), or (III), the production thereof, and the use thereof as matriptase inhibitors, in particular the use thereof as drugs for inhibiting tumor growth and/or metastasization.

21 Claims, No Drawings

META-SUBSTITUTED PHENYL SULFONYL AMIDES OF SECONDARY AMINO ACID AMIDES, THE PRODUCTION THEREOF, AND USE THEREOF AS MATRIPTASE INHIBITORS

The present invention relates to meta-substituted phenyl sulfonyl amides of secondary amino acid amides according to the general formula (I), (II), or (III), the production and use thereof as matriptase inhibitors, particularly the use thereof as medications for inhibiting tumor growth and/or metastasization.

Proteases regulate numerous physiological processes, which enable or stimulate the growth and metastasis of tumor cells. In particular, this concerns the proteolytic degradation of the extracellular matrix proteins surrounding the tumor cells, which enable the invasion of the tumor cells metastasizing from the tumors into the surrounding tissue and the lymph system or the blood system, as the case may be. Proteases are also involved in the activation of growth factors that, for example, stimulate proliferation of tumor cells or angiogenesis, thus enabling tumors to grow. These proteolytic enzymes include different matrix metal proteases, membrane-bound metal proteases, lysosomal cysteine proteases and a variety of serine proteases such as urokinase, plasmin, elastase, thrombin or cathepsin G and also the type II transmembrane serine protease matriptase.

There have been numerous experiments to arrest the growth and metastasizing of tumors through the use of protease inhibitors, but until now, studies using matrix metal proteases inhibitors have not shown any effect in clinical studies (Coussens et al., Science 295, 2387-2392, 2002).

Matriptase is a serine protease similar to trypsin that was originally isolated from breast cancer cells and which mainly breaks down C-terminal peptide compounds of the basic amino acid arginine.

The terms MT-SP1 (membrane-type serine protease 1), TADG-15 (tumor-associated differentially expressed gene-15) or ST14 (suppressor of tumorigenicity 14)/SNC19 have also been used for matriptase in the literature. The term matriptase also comprises the shortened protein forms with proteolytic activity, originated from the break down of proteases normally found in the membrane, and which, in some cases, are no longer found in those membranes.

In 1998, the matriptase gene was cloned as a putative tumor suppressor through a subtractive hybridizing process in which both healthy and carcinogenic intestinal tissues were used (Zhang et al. Cytogenet. Cell Genet. 83, 56-57, 1998).

Matriptase and MT-SP1 have the same cDNA. However, because of alternative splicing, the protein sequence of the matriptase is shortened in 172 amino acids at the N-terminus, in comparison to that of the MT-SP1. The gene for MT-SP1 was isolated from an epithelial cell line derived from a prostate tumor.

In the scope of the present invention, the term "matriptase" describes all trypsin-like proteins, that derive from the gene sequences with the accession numbers AF118224, AF133086, BANKIt257050 and NM021978 (GenBank/EBI Data Bank) and which have already been described earlier (Takeuchi et al., Proc. Natl. Acad. Sci. USA 96, 11054-11061, 1999; Lin et al., J. Biol. Chem. 274, 18231-18236, 1999).

The enzyme is anchored to the membrane of epithelial or cancer cells through a transmembrane domain, whereby the serine protease domain of the matriptase is localized on the cell surface and consequently in the extracellular space. Therefore, it is assumed that the matriptase plays a role in the proliferation and metastasizing of breast cancer cells through the degradation or alteration of the extracellular matrix proteins, the activation of latent growth factors and other proteolytic cascades (Shi et al., Cancer Res. 53, 1409-1415, 1993; Lin et al., J. Biol. Chem. 272, 9147-9152, 1997).

It was possible to isolate Matriptase from human milk, though in this case it was present almost completely as a proteolytically inactive complex with the endogen inhibitor HAI-1 (Lin et al., J. Biol. Chem. 274, 18237-18242, 1999). The matriptase from breast cancer cells is almost a complete contrast as it does not form a complex, thus presents a catalytically active form and is only bound to HAI-1 in a small segment.

In the meantime, potential substrates of matriptase have been described; among others the polyprotein profilaggrin splits into filaggrin monomers that are necessary for a normal development of the epidermis. Additionally, matriptase can activate the pro-form of the hepatocyte growth factor (HGF), which is also described as a scattering factor. Pro-HGF is secreted from cancer or stromal cells in an inactive form as a single chain protein and is transformed in the extracellular space into it's active, double chain protein form (HGF) through the splitting of the C-terminal of Arg495. The cell plasma membrane surface receptor c-Met is activated and phosphorylated at specific tyrosine residues through the binding of HGF. A close correlation between a high expression of c-Met, matriptase and HAI-1 and a poor prognosis in breast cancer patients was demonstrated recently (Kang et al., Cancer Res. 63, 1101-1105, 2003). The study of ovarian tumors also demonstrated an excessive secretion of matriptase. This study showed that, in opposition to the stage I/II tumors, matriptase is almost without exception secreted without HAI-1 in most stage III/IV advanced tumors. This indicates that, in an advanced stage, there is an unbalance between matriptase and the inhibitor HAI-1, through which the proteolytic activity of matriptase is strengthened and in turn, very likely, also the invasive potential of the tumor cells (Oberst et al., Clin. Cancer Res. 8, 1101-1107, 2002).

Besides the activation of pro-HGF, matriptase is possibly also involved in the triggering of the plasminogen activation cascade. Thus matriptase is able to activate pro-urokinase to urokinase (uPA) (Lee et al., J. Biol. Chem. 275, 36720-36725, 2000; Takeuchi et al., J. Biol. Chem. 275, 26333-26342, 2000), which transforms plasminogen into plasmin. Plasmin is the principal activator of the matrix metal proteases that participate in the degradation of the extracellular matrix proteins, which is considered as a prerequisite for metastasization.

Ihara et al. (J. Biol. Chem. 277, 16960-16967, 2002) were able to show that stomach cancer cells secrete enhanced quantities of β1-6-N-Acetylglucosaminyltransferase (GnT-V) which is able to glycosylate matriptase. Through this modification, matriptase becomes resistant to degradation and its proteolytically active form is found in higher concentrations.

From these findings, it can be deduced that the development of an effective and selective matriptase inhibitor may help to arrest the proliferation of tumors and their metastasizing. Even though the x-ray structure of the catalytic domain of matriptase in complex with benzamidine and with bovine pancreatic trypsin inhibitor has also been clarified in the meantime, there are only a few matriptase inhibitors known until now (Friedrich et al., J. Biol. Chem. 277, 2160-2168, 2002).

Enyedy et al. (J. Med. Chem. 44, 1349-1355, 2001) described bis-benzamidine, where the most effective inhibitor features a Ki value of 0.19 µM.

The international patent application WO 01/97794 describes a method to inhibit the progression of a carcinoma, in which matriptase plays a role. Thereby compounds were established, that possess two groups that are capable of becoming positively charged under a physiological pH value. These groups are linked with each other through a chemical structure unit that has a length of 5 to 30, commonly 15 to 24 angstroms. Amino, amidino, and guanidino groups, as well as a cyclic group derived from the amidino or, as the case may be, guanidino groups were disclosed as being positively charged. Amino acid derivates are not mentioned in the WO 01/97794, specifically no sulfonylated amino acid derivates. In fact, the compounds that are explicitly disclosed in the WO 01/97794 are fundamentally different to those claimed in the scope of the present invention.

Tripeptide aldehydes with a C-terminal arginal were published in WO 02/20475. After a pre-incubation of matriptase with these inhibitors over a time period of 30 minutes, IC50 values of less than 100 nM were determined for the most effective compounds, although exact inhibition constants were not stated. These inhibitors probably bind in a covalent manner to matriptase by the formation of a hemiacetal. In the case of the development of inhibitor factors for other trypsin-like serine proteases, such as, for example, thrombin or Xa factor, it was shown, however, that such peptide aldehydes transition state analogues are not suitable for the development of an active ingredient to be used in medicine. Recently it was shown that the growth of androgen-independent tumors can be reduced through intraperitoneal administration of the arginal derivate CVS-3983 (Galkin et al., The Prostate 61, 228-235, 2004). These authors described more tripeptide-derived substrate analogues, in which the C-terminal arginal is substituted by a chain of P1-residues, which enables binding to the S1 pocket of the enzyme (WO 2004/058688).

Long et al. (Bioorganic. Med. Chem. Lett. 11, 2515-2519, 2001) published the synthesis of a bicyclical peptide of 14 amino acids that was isolated originally from sunflower seeds. The peptide inhibits matriptase with an inhibition constant of 0.92 nM; however, this makes one assume that this structure, because of its low specificity, is not appropriate for clinical development. Further redox stable derivates of these peptides with lower activity were described briefly in Jiang et al., Organic Lett. 9, 9-12, 2007.

In WO 2004/101507 were described sulfonylated derivates of 3-amidino-phenylalanines, where the C-terminal is modified with a secondary amide that necessarily possesses in turn a basic substituent. The most effective compounds inhibit matriptase with Ki values of <5 nM (Steinmetzer et al., J. Med. Chem. 49, 4116-4126, 2006). A disadvantage of this particularly effective compound with Ki values <10 nM is that, because of its three charged, strong basic groups in the N and C-terminal residues, as well as in the central amino acid building blocks, and its derived hydrophilic properties, it is absorbed only in very small quantities after oral administration in research animals, and it shows a short retention time in the circulation after intravenous administration in rats, in the majority of cases.

One of the underlying goals for the present invention was to obtain an active ingredient that was also appropriate for therapeutic applications, had enhanced properties, and was ready to use, particularly for oral administration, that inhibits matriptase with a higher activity and specificity and that possesses a lower basicity.

Surprisingly, it was found that meta-substituted phenyl sulfonyl amides of secondary amino acid amides work as inhibitors of matriptase, even when they do not possess any basic residues anymore in their N-terminal sulfonyl residues or in their C-terminal secondary amide residues.

Additionally, it was found that in this type of structure the central 3-amidino-phenylalanine can be replaced by the less strongly basic 3-amino methyl phenylalanine, and that it nevertheless maintains its matriptase inhibiting factor.

A purpose of the present invention is therefore a compound according to the formula (I)

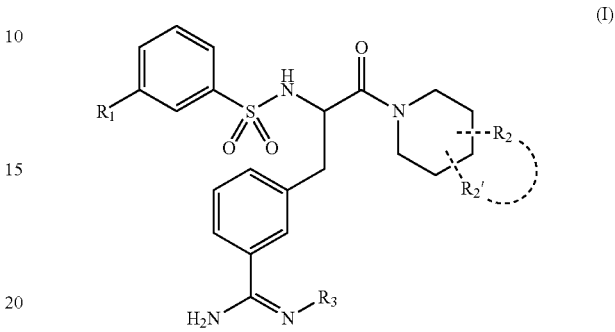

or a salt from this compound, whereas $R_1$ a simple or multiple substituted ring structure is selected from an aryl residue or a heteroaryl residue that also can be partially or wholly hydrogenated, particularly a non-hydrogenated aryl residue or a non-hydrogenated heteroaryl residue, for example a heteroaryl residue with one or two atoms of nitrogen, selected preferentially from a phenyl residue, pyridyl residue, pyrimidine residue, indole residue, tetrahydropyridyl residue, particularly an amino tetrahydropyridyl residue, piperidinon residue or pyridazinone residue; and $R_2$ and $R_2'$, inasmuch as they are present alone or cojoined, each independently of the other are a ramified or straight chain alkyl residue with 1-6, primarily 2-4, particularly 2 carbon atoms, where one or more methylene groups can be replaced by heteroatoms, such as oxygen or nitrogen; a ramified or straight chain, preferably a straight chain, amino alkyl residue or guanidine alkyl residue with 1-6, primarily 2-4, particularly 2 carbon atoms, above all a straight chain amino alkyl residue; or —$(CH_2)_m$—C(=O)—$NHR_4$ where m equals a whole number from 0 to 4, particularly equal to 0 or 3, and $R_4$ is a hydrogen or a —$(CH_2)_k$—$CH_3$ residue with k being equal to a whole number from 0 to 3, particularly 0; preferably only $R_2$ is present; or $R_2$ and $R_2'$ build a ring structure that, together with the piperidide, forms for example the following structure elements:

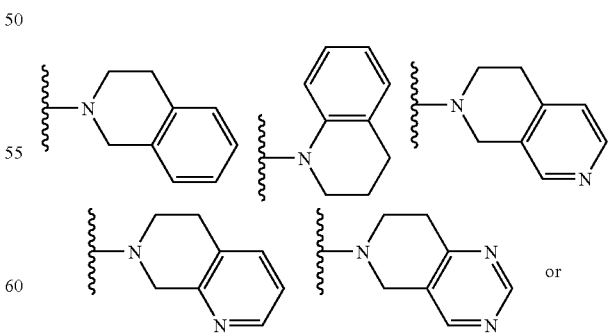

$R_1$ is a ramified or straight chain, primarily a straight chain amino alkyl residue, hydro alkyl residue with 1 to 6, primarily 1 to 4, particularly 2 to 4 carbon atoms; or a 3-azetidin-C(=O)—NH-residue; in particular, $R_1$ is the named amilo alkyl residue, above all an unramified n-amino butyl residue, or the 3-azetidin-C(=O)—NH-residue; and $R_2$ and $R_2'$, inasmuch as they are present alone or cojoined, each independently of the other are a ramified or straight chain, primarily a straight chain aminoalkyl residue or guanidino alkyl residue with 1-6, primarily 1-4, particularly 2-4 carbon atoms, above all a straight chain aminoalkyl residue, particularly a straight chain amino ethyl residue; or $R_2$ is —(CH$_2$)$_m$—C(=O)—NHR$_4$ where m equals a whole number from 0 to 4, particularly equals 0 or 3, and $R_4$ is a hydrogen or a —(CH$_2$)$_k$—CH$_3$ residue where k equals a whole number from 0 to 3, particularly 0; in particular $R_2$ is the mentioned amino alkyl residue; particularly only $R_2$ is present;

or $R_1$ is an H$_2$N—(CH$_2$)$_n$—C(=O)—NH-residue, a HO—(CH$_2$)$_n$—C(=O)—NH-residue where n equals a whole number from 1 to 4, primarily 2 or 3, particularly 2; or a 3-azetidin-C(=O)—NH-residue; in particular, $R_1$ is the named H$_2$N—(CH$_2$)$_n$—C(=O)—NH-residue; and $R_2$ and $R_2'$, inasmuch as they are present alone or cojoined, each independently of the other are a non-basic residue, particularly $R_2$ is selected from the following residues:

—(CH$_2$)$_m$—C(=O)—NHR$_4$ where m equals a whole number from 0 to 4, particularly equals 0 or 3, and $R_4$ is a hydrogen or a —(CH$_2$)$_k$—CH$_3$ residue with k being equal to a whole number from 0 to 3, particularly 0; or —(CH$_2$)$_o$—C(=O)—OR$_5$ where o is a whole number from 1 to 6, primarily 1 to 4, particularly 3 and $R_5$ is a hydrogen or a ramified or straight chain alkyl group with 1 to 4, primarily 1 or 2 carbon atoms, particularly a straight chain alkyl group;

or $R_2$ and $R_2'$ build a ring structure that, together with the piperidide, builds for example one of the structure elements named above;

and

In all abovementioned cases, $R_3$ is hydrogen, a hydroxyl group, an alkoxy group, an acetyloxy group or an alkyloxycarbonyl group, whereas the alkyl residue has 1-6 carbon atoms, principally $R_3$ is a hydrogen or a hydroxyl group, particularly hydrogen.

Preferred compounds, for example, are compounds in which $R_2'$ is not present and in which $R_1$ is selected from a simple or, as the case may be, multiple substituted phenyl residue, piridyl residue, pyrimidine residue, indole residue, tetrahydropyridyl residue, particularly an amino tetrahydropyridyl residue, piperidinone residue or pyridazinone residue; and $R_2$ is a straight chain aminoalkyl residue with 1-6, primarily 2-4, particularly 2 carbon atoms; or —(CH$_2$)$_m$—C(=O)—NHR$_4$ where m equals a whole number from 0 to 4, particularly equals 0 or 3, and $R_4$ is a hydrogen or a —(CH$_2$)$_k$—CH$_3$ residue where k equals a whole number from 0 to 3, particularly 0;

or $R_1$ and $R_2$ are a straight chain aminoalkyl residue with 1 to 6, primarily 1 to 4, particularly 2 to 4 carbon atoms, particularly $R_1$ is an unramified n-amino butyl residue;

or $R_1$ is a H$_2$N—(CH$_2$)$_n$—C(=O)—NH-residue where n equals a whole number from 1 to 4, primarily 2 or 3, particularly 2; and $R_2$ is selected from among the following residues:

—(CH$_2$)$_n$—C(=O)—NHR$_4$ where m equals a whole number from 0 to 4, primarily equals 0 or 3, and $R_4$ is a hydrogen or a —(CH$_2$)$_k$—CH$_3$ residue where k equals a whole number from 0 to 3, particularly 0; or —(CH$_2$)$_o$—C(=O)—OR$_5$ where o is a whole number from 1 to 6, primarily 1 to 4, particularly 3 and $R_5$ is a hydrogen or a straight chain alkyl group with 1 to 4, primarily 1 or 2 carbon atoms;

and

In all the above mentioned cases, $R_3$ is hydrogen, a hydroxyl group, an alkoxy group, an acetyloxy group or an alkyloxycarbonyl group, whereas the alkyl residue contains 1-6 carbon atoms, primarily $R_3$ is a hydrogen or a hydroxyl group, particularly hydrogen.

Particular preference is given to a compound according to the formula (I) in which the residue $R_2$ is present in meta or para position, particularly in para position, or when $R_2$ as well as $R_2'$ are present, in which the residue $R_2$ is found in para position and the residue $R_2'$ in ortho or meta position.

It is additionally advantageous, when the ring structure from the residue $R_1$ is substituted in the meta and/or para position. The following residues are the preferred substituents in the ring structure of residue $R_1$: $R_6$—O— where $R_6$ is a ramified or straight chain alkyl residue with 1 to 6, particularly 1 to 4, particularly 1 to 3 carbon atoms; (CH$_3$)—(CH$_2$)$_p$— where p equals a whole number from 0 to 6, particularly 0 to 2, particularly 1; a halogen, preferably chlorine; and/or an amino group.

The substitution on the phenyl residue is selected mainly from the following residues: $R_6$—O— where $R_6$ is a ramified or straight chain alkyl residue with 1 to 6, particularly 1 to 4, particularly 1 to 3 carbon atoms; (CH$_3$)—(CH$_2$)$_p$— where p equals a whole number from 0 to 6, particularly 0 to 2, particularly 1; and/or a halogen, preferably chlorine;

The substitution on the pyridyl residue, on the pyrimidine residue or on the tetrahydropyridyl residue is selected mainly from the following residues: (CH$_3$)—(CH$_2$)$_p$— where p equals a whole number from 0 to 6, particularly 0 to 2, particularly 1; and/or an amino group, above all the substitution on the pyrimidine residue or on the tetrahydropyridyl residue is an amino group. It is particularly preferred when the substitution on the pyrimidine residue is a (CH$_3$)—(CH$_2$)$_p$-group, where p equals a whole number from 0 to 6, particularly 0 to 2, particularly 1, and is above all a methyl group.

A further purpose of the present invention is a compound according to the formula (II)

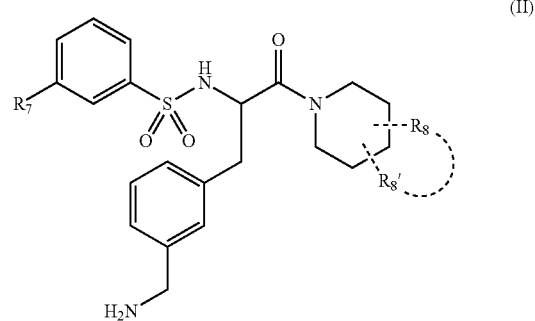

(II)

or a salt from this compound, where $R_7$ has a simple or, as the case may be, multiple substituted ring structure, and is selected from an aryl residue or a heteroaryl residue that is partially or, as the case may be, wholly hydrogenated, particularly a heteroaryl residue with one or two nitrogen atoms, primarily selected from a phenyl residue, pyridyl residue, pyrimidine residue, indole residue, tetrahydropyridyl residue, piperidinon residue or pyridazinone residue; a ramified or unramified alkyl residue with 1-8 carbon atoms, whereas one or more methyl groups can be replaced by heteroatoms, particularly oxygen or nitrogen; a H$_2$N—(CH$_2$)$_r$—C(=O)—NH-residue, a HO—(CH$_2$)$_r$—C(=O)—

NH-residue, a $NH_2$—$(CH_2)_q$-residue, or a HO—$(CH_2)_q$—residue, where r equals a whole number between 1 and 4, primarily 2 or 3, particularly 2 and, each independently of the other, q equals a whole number between 1 and 5, particularly 4 or 5, principally 4; or a 3-azetidin-C(=O)—NH-residue, particularly the aforementioned aryl residue; and $R_8$ and $R_8'$, inasmuch as they are present alone or cojoined, each independently of the other is a ramified or straight chain, primarily a straight chain alkyl residue, with 1-8 carbon atoms, whereby one or more methylene groups can be replaced by heteroatoms, primarily oxygen or nitrogen; an amino alkyl residue or guanidino alkyl residue with 1-6, primarily 2-4, particularly 2 carbon atoms each; or a —$(CH_2)_m$—C(=O)—$NHR_4$ where m equals a whole number from 0 to 4, particularly equals 0 or 3, and $R_4$ is a hydrogen or a —$(CH_2)_k$—$CH_3$ residue where k equals a whole number from 0 to 3, particularly 0; primarily the aforementioned aminoalkyl residue; or $R_8$ and $R_8'$ build a ring structure that builds, together with the piperidide, for instance a structure element like the one defined above.

Preference is given to compounds in which $R_8'$ is not present and $R_7$ is a simple or, as the case may be, multiple substituted ring structure, selected from a phenyl residue, pyridyl residue, pyrimidine residue, indole residue, tetrahydropyridyl residue, piperidinon residue or pyridazinone residue; a $H_2N$—$(CH_2)_r$—C(=O)—NH-residue, where r equals a whole number from 1 to 4, primarily 2 or 3, particularly 2; and $R_8$ is an aminoalkyl residue with 1-6, primarily 2-4, particularly 2 carbon atoms each.

In particular, $R_7$ is a simple substituted phenyl residue or, as the case may be, an $NH_2$—$(CH_2)_r$—C(=O)—NH-residue and r has the meaning designated above.

In further preferred compounds, the residue $R_8$ is found in the para position of the piperidine ring. If present, the residue $R_8'$ can be found in the ortho or meta position of the piperidine ring.

In further compounds, the substitution at $R_7$ is primarily selected from the following residues: $R_{10}$—O— where $R_{10}$ is a ramified or straight chain alkyl residue with 1 to 6, primarily 1 to 4, particularly 1 to 3 carbon atoms, or $(CH_3)$—$(CH_2)_s$— where s equals a whole number from 0 to 6, primarily 0 to 2, particularly 1, or an amino group. In particular, the substitution on the phenyl residue is a $R_{10}$—O-residue where $R_{10}$ is a ramified or straight chain alkyl residue with 1 to 6, primarily 1 to 4, particularly 1 to 3 carbon atoms, above all 1 carbon atom.

An additional purpose of the present invention is a compound according to the formula (III)

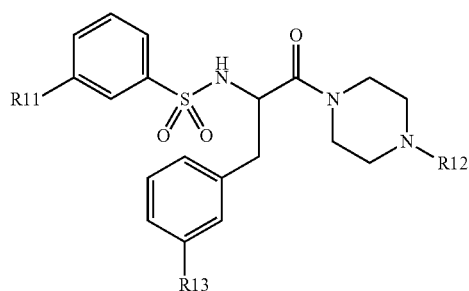

(III)

or a salt from this compound, where

R11 is an $NH_2$—$(CH_2)_v$—C(=O)—NH-residue where v equals a whole number from 1 to 4, primarily 2 or 3, particularly 2; a 3-azetidine-C(=O)—NH-residue, a simple or, as the case may be, multiple substituted ring structure is selected from an aryl residue or a heteroaryl residue, that can also be partially or wholly hydrogenated, particularly a non-hydrogenated aryl residue or a non-hydrogenated heteroaryl residue, for instance a heteroaryl residue with one or two nitrogen atoms, primarily selected from a phenyl residue, pyridine residue, pyrimidine residue, indole residue, tetrahydropyridyl residue, piperidinone residue or pyridazinone residue; R11 is primarily the aforementioned $NH_2$—$(CH_2)_v$—C(=O)—NH-residue;

R12 is hydrogen; a ramified or straight chain, primarily a straight chain amino alkyl residue with 1 to 6, primarily 1 to 4, particularly 2 to 4, above all with 2 carbon atoms; a —C(=O)—O—R14 group, —C(=O)—R14 group or —C(=O)—NH—R14 group with, in each case, R14 independently from each other equaling an alkyl residue with 1 to 6, primarily 1 to 4, particularly 2 carbon atoms; or an aralkyl or heteroaralkyl residue with 4-12, particularly 5-6 carbon atoms each in their aryl or heteroaryl segments, whereby the heteroaryl segment of the heteroaralkyl residue can have 1 to 2, particularly 1 heteroatom, above all nitrogen, and with 1 to 6, primarily 1 to 4, particularly 2 to 4, above all 1 or 2 carbon atoms each in the alkyl residue, particularly a benzyl residue; and R13 is an amino methyl residue or a substituted or unsubstituted amidino residue of the formula —C(=NR15)$NH_2$ where R15 equals a hydrogen, a hydroxyl group, an alkoxy group, an acetyloxy group or an alkyloxycarbonyl group, whereby the alkyl residue contains 1-6 carbon atoms, R15 is preferably a hydrogen or a hydroxyl group, particularly hydrogen.

Preferred compounds are compounds, in which

R11 is an $NH_2$—$(CH_2)_v$—C(=O)—NH-residue where v equals a whole number from 1 to 4, primarily 2 or 3, particularly 2;

R12 is hydrogen; a straight chain aminoalkyl residue with 1 to 6, primarily 1 to 4, particularly 2 to 4, above all 2 carbon atoms; or a —C(=O)—O—R14 group each with R14 independently from each other being equal to a straight chain alkyl residue with 1 to 6, primarily 1 to 4, particularly 2 carbon atoms; or a benzyl residue; and R13 is an amino methyl residue or a substituted or unsubstituted amidino residue of the formula —C(=NR15)$NH_2$ where R15 equals a hydrogen, a hydroxyl group, an alkoxy group, an acetyloxy group or an alkyloxycarbonyl group, whereby the alkyl residue contains 1-6 carbon atoms, R15 is preferably a hydrogen or a hydroxyl group, particularly hydrogen.

Notably preferred compounds in the present invention are the compounds according to the examples or compounds derived from the individual examples in the scope of the general formulas (I), (II) or (III). Most preferable in this case are the compounds or compound classes with a Ki value smaller or equal to 100 nM, primarily those smaller than or equal to 65 nM, particularly those smaller than 31 nM, above all those smaller than 15 nM. Furthermore, the uncharged or weak basic compounds are particularly preferred for oral administration, as these are better administered orally than the corresponding, more strongly charged compounds. Compounds containing a benzamidine group are primarily used in their pro-drug forms, because it is not until they are in the body that they are converted into an amidino group. Appropriate benzamidine pro-drugs are compounds with a hydroxy amidino, acyl amidino, alkyloxy carbonyl amidino or alkoxy amidino group.

The corresponding salts of the compounds according to the general formula (I), (II) or (III) are easily extracted with aid of the corresponding organic or inorganic acids, for example with trifluoroacetic acid, hydrochloric acid, succinic acid, acetic acid, or fumaric acid.

In a particular embodiment, the compounds according to the invention can be covalently coupled (PEGylation), either directly through functional groups or indirectly with the aid of a link to polyethylenglycol (PEG), for example at PEG with 5-10 kDa using methods known to the experts. This achieves, for example, a longer half-life period of the above mentioned compounds in the patient. An alkyl chain with e.g. 2-6 carbon atoms and its corresponding functional groups, as shown in the examples, for example, qualifies as a link. Particularly, a polyethylene glycol chain is covalently coupled with the compounds according to the invention at the residues $R_1$, $R_2$, $R_2'$, $R_7$, $R_8$, $R_8'$, $R_{11}$ and/or $R_{12}$, particularly with help of an alkyl chain with 2-6 carbon atoms and an amide compound.

In general, compounds with a central L-configuration are preferred. The following methods qualify as suitable production methods here—these are also appropriate for the production of racemics, whereby they are used particularly for the synthesis of enantiomer-pure 3-cyanophenylalanine.

The compounds that correspond with the invention according to the formula (I) where R2 is an amino alkyl residue, are commonly produced using a method in which, for example, a protected or unprotected, substituted piperidide, such as a 3-(halogen, preferably bromine or amino)-phenylsulfonyl-3-cyanophenylalanyl-4(2-protected amido alkyl)piperidide at the meta position of the phenyl residue is derived with a protected R1 residue, and subsequently the cyano group is transformed with hydroxylamine into hydroxylamidine, which can then be hydrogenated to amidine. The hydrogenation can take place either directly or after replacement with, for example, acetic anhydride. At the end of the synthesis one or possibly more existing protection groups are divided. For example, it can also originate from a 3-(halogen, preferably bromine or amino)-phenylsulfonyl-3-cyano-phenylalanine, which is replaced by a protected amido alkyl piperidide. Corresponding alternative methods can be deduced easily from the examples by an expert.

The compounds that correspond with the invention according to the formula (I) in which R2 is a non-basic residue, can generally be produced following a method in which a phenyl sulfonyl-3-cyanophenylalanine substituted in 3-position with a halogen, a nitro or an amino group is replaced by a substituted piperidin derivate, e.g. N-methyl-4-(piperidine-4-yl) butanamide, after which, the possibly present nitro group is reduced into an amino group, and then a suitable R1 residue is coupled directly or in a protected form, at the halogen or amino aromatic compound substituted in 3-position. Subsequently, the amidino group is built as described above. At the end of the reaction chain, any remaining protection groups can be divided. Again, corresponding alternative methods can be deduced easily from the examples by an expert.

The compounds that correspond with the invention according to the formula (II) can generally be produced following a method in which a protected or unprotected aryl sulfonyl-1-(3-amidinophenylalanine or an arylsulfonyl-3-aminoalkyl phenylalanine, protected at the amino group, and particularly a protected arylsulfonyl-3-aminomethyl phenylalanine, is replaced by a substituted piperidine and accordingly derived. In this case too, an expert can easily deduce alternative methods from the examples.

The compounds that correspond with the invention according to the formula (III) can be produced in general following a method in which a protected or unprotected aryl sulfonyl-1-(amidino or a 3-alkylamino protected at the amino group) phenylalanine, particularly a protected arylsulfonyl-3-aminomethyl phenylalanine, is replaced by a protected or substituted piperazine and accordingly derived. Again, corresponding alternative methods can be deduced easily from the examples by an expert.

The protection groups can each be a tertiary butyloxycarbonyl group or a benzyloxycarbonyl group.

A further goal of the present invention is a medication containing at least one of the compounds that correspond with the invention. The medication can be used, for example, in the form of a tablet, a coated pill, a capsule, a pellet, a suppository, a solution, particularly an injectable or infusion solution, eye, nose or ear drops, a syrup, an emulsion or suspension, a globule, a stylus, an aerosol, a powder, a paste, a lotion or a salve.

The medications according to the invention or rather the compounds that correspond with the invention are particularly suited for the therapy or prophylaxis of a tumor, particularly for oral, subcutaneous, intravenous or transdermal administration. Above all, it is possible herewith to achieve a reduction in the formation of tumor metastasis. A further general use of the medications and compounds that correspond with the invention concerns the inhibition of matriptase. On this basis, the present invention also extends to the in-vitro use of a compound according to the invention for inhibition of matriptase.

The quantity of the compound according to the invention that is necessary to achieve the desired biological effect depends on a series of factors, e.g. the specific compound selected, the proposed use, the administration type and the clinical status of the patient.

In general, the daily dosage varies from 0.05 mg to 50 mg per day and per kilogram of body weight (typically from 0.5 mg to 20 mg per day and per kilogram of body weight), e.g. 1-10 mg per day and per kilogram of body weight. An intravenous dose can range from 0.05 mg to 10.0 mg/kg, which can be administered suitably as infusion with 10 ng to 100 ng per kilogram per minute. Appropriate infusion solutions for this purpose can contain e.g. between 0.1 ng and 10 mg, typically between 1 ng and 10 mg per milliliter. Single doses can contain e.g. between 1 mg and 5 g of the active ingredient. Therefore, ampules for injection can contain for example between 1 mg and 100 mg, and single-dose preparation for oral use, such as tablets or capsules, may contain for example between 1.0 and 1000 mg, typically between 10 and 600 mg. In the case of pharmaceutically compatible salts, the aforementioned weight specifications apply to the weight of the underlying free compounds in the salt. The compounds that correspond with the invention can be used as such for prophylaxis or therapy of the above named conditions, though they are primarily presented with a compatible excipient or vehicle in the form of a pharmaceutical composition. Of course, the excipient or vehicle must be well-suited, in the sense that it is compatible with other ingredients of the composition and that it is not harmful to the health of the patient.

The excipient can be a solid or a liquid or both and is formulated primarily with the compound as a single dose, for example as a tablet, which can contain between 0.05% and 95% wt % of the active ingredient. Further pharmaceutically active substances can also be present, including further compounds that correspond with the invention. The medications according to the invention can be manufactured following one of the known pharmaceutical methods, which essentially require that the ingredients are treated with pharmacologically compatible excipients and/or vehicles.

Pharmaceutical compositions according to the invention are particularly those that are suitable for oral, rectal, topical, peroral (e.g. sublingual) and parenteral (e.g. subcutaneous, intramuscular, intradermal or intravenous) administration, even though the most suitable method of application depends, in every single case, on the type and severity of the condition to be treated and from the type of each of the compounds that correspond with the invention to be used. Preparations for coated pills and extended release coated pills are also included in the scope of the finding. Acid and gastric juice-resistant preparations are preferred. Suitable gastric juice-resistant coatings include cellulose acetate phthalate, polyvinyl acetate phthalate, hydroxypropyl methyl cellulose phthalate and anionic polymers from methacrylic acid and methacrylic acid methyl ester.

Suitable pharmaceutical compounds for oral use that are particularly preferred can be presented as individual units, such as caplets, oblate caplets, lozenges or tablets, each containing a specific amount of the compound according to the invention; as powder or granulate; as solution or suspension in an aqueous or non-aqueous liquid; or as an oil-in-water or water-in-oil emulsion. As already stated, these compositions can be prepared according to any suitable pharmaceutical method, which includes a step in which the excipient and the vehicle (which can be composed by one or more additional ingredients) come in contact with one another. In general, the preparations can be produced through uniform and homogenous mixing of the active ingredient with a liquid and/or a finely distributed solid excipient, whereby the product, if necessary, is shaped.

For example, a tablet can be produced using this method, wherein the compound is compressed as powder or granulate or shaped with one or more additional ingredients, as the case may be. Compressed tablets can also be produced in a suitable machine by pelletizing the compound in free flowing form, for example as a powder or granulate treated with a binder, glidant, inert diluent and/or one (more) surface-active/disintegrant agents, as the case may be. Shaped tablets can be produced in a suitable machine by molding the powder with a compound moistened with an inert aqueous diluting agent.

Pharmaceutical compositions suitable for peroral (sublingual) use include lozenges, which contain a compound according to the invention as well as a flavoring agent, generally saccharose or gum arabic or tragacanth, and tablets that include the administration of an inert base like Gelatin and glycerin or saccharose and gum arabic.

Suitable pharmaceutical compositions for parenteral use include primarily sterile, aqueous compositions of a compound according to the invention, which are primarily isotonic with the blood of the intended recipient. These preparations are primarily administered intravenously, even though the administration can also be performed as a subcutaneous, intramuscular or intradermal injection. These preparations can be produced primarily by mixing the compound with water and the resulting solution is made sterile and isotonic with blood. Injectable medications according to the invention generally contain between 0.1 and 5 wt % of the active compound. With respect to further preparation, please refer to the current manuals.

Thus, the invention also includes a method for the preparation of a medication, in which one or more compounds that correspond with the invention are treated with suitable excipients and vehicles, as described above.

The following methods and examples serve as a detailed explanation of the invention, without constraining it.

Methods to Analyze the Compounds that Correspond with the Invention

Analytical HPLC

Analytical reversed-phase-HPLC was performed using a HPLC pump model LC-10A from the company Shimadzu, composed of the system parts CTO-10AS column oven, LC-10AD pumps (2×), DGU-14A degasser, SIL-10AD autoinjector, SCL-10A system controller, SPD-10A UV-Vis detector and a Luna 5 µm C18 column (2) 100 Å, 250×4.6 mm from the company Phenomenex, using the associated software Shimadzu CLASS-VP, Version 5.3. The detection took place at 220 nm. Water with 0.1% TFA (A) and acetonitrile with 0.1% TFA (B) at a flow rate of 1 ml/ml and a linear gradient (1% B/min) were used as diluting media. All polyethylenglycol-modified active ingredients were analyzed with a Jupiter 5 µm C18 column (2) 300 Å, 250×4.6 mm from the company Phenomenex.

Preparative HPLC

Preparative RP-HPLC was performed using a HPLC pump from the company Shimadzu, composed of the system parts LC-8A preparative pumps (2×), DGU-14A degasser, FRC-10A fraction collector, SCL-10A system controller, SPD-10A UV-Vis detector and a Luna 5µ C8 Column (2) 100 Å, 250×30.0 mm from the company Phenomenex, using the associated software Shimadzu CLASS-VP, Version 5.3. The detection took place at 220 nm. Likewise, water with 0.1% TFA (A) and acetonitrile with 0.1% TFA (B) at a flow rate of 10 or 20 ml/ml and a suitable gradient were used as diluting media.

Mass Spectroscopy

The mass spectra were measured in a standard manner on an ESI-MS LCQ from the company Finnigan (Bremen, Germany). All of the polyethylenglycol-coupled compounds were analyzed on a Maldi Ultraflex TOF/TOF instrument from the company Bruker.

Thin-Film Chromatography

For the thin-film chromatography, ready-to-use silica gel Adamant $UV_{254}$ plates from the company Macherey-Nagel were used. A mixture of n-butanol, glacial acetic acid and water (4:1:1) was used as eluent. The detection of the compounds was achieved through UV-absorption at 254 nm, additionally a ninhydrin solution (300 mg ninhydrin dissolved in 100 ml n-butanol and 3 ml acetic acid) and, after incubation of the DC plate in chlorine atmosphere, a o-tolidine solution (150 mg o-tolidine and 2.1 KI dissolved in 2 ml acetic acid and 148 ml water) were used as spraying reagents.

Abbreviations Used

Ac Acetyl
ACN Acetonitrile
Ame Aminomethyl
Boc tert-butyloxycarbonyl
Bz Benzoyl
Bzl Benzyl
Bzls Benzyl sulfonyl
Cbz Benzyloxycarbonyl
CKIBE Chlorcarbonic acid isobutyl ester
Dap α,β-diaminopropionicacid
DIEA Diisopropylethylamine
DCM Dichloromethane
DMF N,N-Dimethylformamide
HPLC High-performance liquid chromatography
iNip Isonipecotin acid
iPr iso-propyl
u.V. under Vacuum
SV Solvent
MS Mass Spectroscopy
n.d. Not determined
Nip Nipecotic acid
NMM N-Methyl morpholine
PEG Polyethylene glycol
PyBop Benzotriazole-1-yl-N-oxy tris(pyrrolidino)phosphonium hexafluorophosphate
Pzd piperazide
RT Room temperature Suc Succinyl
tBu tert-butyl
TEA Triethylamine
Tfa Trifluoroacetyl
TFA Trifluoroacetic acid

EXAMPLES

Example 1

3-(3,4-dimethoxyphenyl)phenyl sulfonyl-d/l-Phe(3-Am)-4-(2-amino ethyl)piperidide×2 TFA

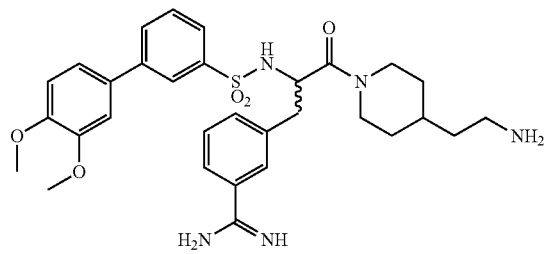 [SMILES: COc1ccc(-c2cccc(S(=O)(=O)NC(Cc3cccc(C(=N)N)c3)C(=O)N3CCC(CCN)CC3)c2)cc1OC]

1a) 3-Brom phenyl sulfonyl-d/l-Phe(3-CN)—OH

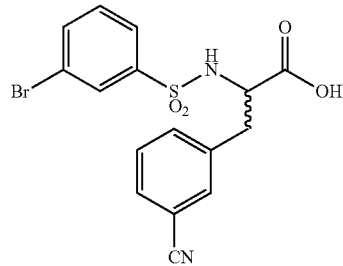 [SMILES: N#Cc1cccc(CC(NS(=O)(=O)c2cccc(Br)c2)C(=O)O)c1]

1 g (5.26 mmol) H-d/l-Phe(3-CN)—OH (Senn Chemicals AG, Dielsdorf, Switzerland) is suspended in 20 ml water and 4 ml dioxane and treated with 1.006 ml (5.78 mmol) DIEA. Under ice cooling, 1.478 g (5.78 mmol) 3-bromphenyl-sulfonyl chloride (Alfa Aesar), dissolved in 16 ml dioxane, is added dropwise within 30 min. The pH is assessed and adjusted to 8-9 through an additional application of DIEA. It is stirred one hour longer at 0° C. and overnight at room temperature. The solvent is removed through a vacuum and the remainder is dissolved in water through addition of 1 N NaOH (pH ca. 10). The aqueous phase is extracted once with ethyl acetate and acidified with 6 N HCl (pH ca. 2). The aqueous phase is extracted 3 times with ethyl acetate. Subsequently, the ethyl acetate is washed 3 times with saturated NaCl solution, the SV dried with $Na_2SO_4$ and removed through a vacuum.

Yield: 1.9 g (4.64 mmol) yellowish solid
HPLC: 49.2% B 1b) 3-bromophenyl sulfonyl-d/l-Phe(3-CN)-4-(2-Boc-amidoethyl)piperidide

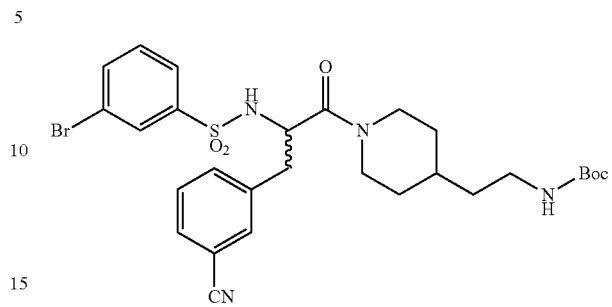

1.5 g (3.66 mmol) 3-bromophenyl sulfonyl-d/l-Phe(3-CN)—OH and 837 mg (3.66 mmol) 4-(2-Boc-amidoethyl) piperidide (Steinmetzer et al., J. Med. Chem. 49, 2006, 4116) are dissolved in 10 ml DMF by adding 1.27 ml (7.32 mmol) DIEA, and mixed at 0° C. with 1.9 g (3.66 mmol) PyBop. The reaction solution is stirred for 30 min at 0° C. and 3 h at RT and the SV is removed through a vacuum. The remainder is extracted in EE and washed 3 times with 5% $KHSO_4$-solution, 1 time with saturated NaCl solution, 3 times with saturated $NaHCO_3$— solution and 3 times with saturated NaCl solution. The SV is dried with $Na_2SO_4$ and extracted under vacuum. The residual remainder is purified by means of preparative HPLC and the solvent is extracted u.V.

Yield: 1.35 g oil
HPLC: 64.16% B 1c) 3-(3,4-dimethoxyphenyl)phenyl sulfonyl-d/l-Phe(3-CN)-4-(2-Boc-amidoethyl)-piperidide

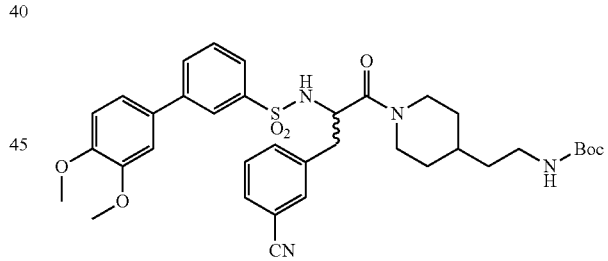

67.1 mg (0.108 mmol) 3-bromophenyl sulfonyl-d/l-Phe(3-CN)-4-(2-Boc-amidoethyl)piperidide and 29.6 mg 3,4-dimethoxyphenylboronic acid (Acros) are treated with 3 ml Toluol and 200 µl of a 2 M $Cs_2CO_3$-solution. Following the addition of ca. 1 mol % Pd-(II)-acetate and ca. 2 mol % 2-dicyclohexylphosphine-2',6'-dimethoxybiphenyl (S-Phos, Aldrich), the reaction solution is heated under argon and 3 h under flow back The reaction solution is centrifuged and the SV of the supernatant is removed u.V. The remainder is dissolved in ethyl acetate and washed twice with half-saturated NaCl solution. The ethyl acetate is dried with $Na_2SO_4$ and removed u.V.

Yield: 40 mg oil
HPLC: 64.39% B, MS ber.: 676.29; gef.: 577.3 $(M+H)^+$ after Boc-splitting off with TFA.

1d) 3-(3,4-dimethoxyphenyl)phenyl sulfonyl-d/l-Phe(3-acetyl hydroxyamidine)-4-(2-Boc-amidoethyl)piperidide

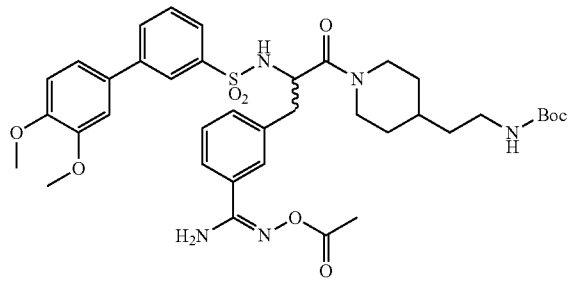 [SMILES: COc1ccc(-c2cccc(S(=O)(=O)NC(Cc3cccc(/C(N)=N\OC(C)=O)c3)C(=O)N3CCC(CCNC(=O)OC(C)(C)C)CC3)c2)cc1OC]

40 mg of the raw product in 3-(3,4-dimethoxyphenyl)phenyl sulfonyl-d/l-Phe(3-CN)-4-(2-Boc-amidoethyl)piperidide is dissolved in 1.5 ml absolute ethanol and treated with 12.2 (0.175 mmol) hydroxylamine×HCl and 30.4 μl (0.175 mmol) DIEA. The reaction solution is stirred 4 h under flow back and overnight by RT (HPLC: 48.9% B). The SV is removed u.V., the remainder dissolved in 1 ml acetic acid and treated with 15 μl acetic acid anhydride. After 30 min the SV is removed u.V. (oil, contains salts).
HPLC: 58.37% B 1e) 3-(3,4-dimethoxyphenyl)phenyl sulfonyl-d/l-Phe(3-Am)-4-(amino ethyl)piperidide×2 TFA The raw product 1d is dissolved in 5 ml 90% acetic acid and hydrogenated overnight with hydrogen and ca. 5 mg 10% palladium from activated carbon as catalyst. The catalyst is filtered out, the SV removed u.V. and the remainder (HPLC: 48.33% B) treated with 1.5 ml TFA. The SV is removed u.V. after 1 hour and the remainder is purified with preparative HPLC.
Yield: 17.5 mg white lyophilized powder
HPLC: 31.48% B, MS ber.: 593.27 gef.: 594.3 (M+H)$^+$ Examples 2-15

In a similar manner, using the corresponding commercially available boronic acid or boronic acid-pinacol ester, further inhibitors were synthesized (Table 1):

TABLE 1

| Example/Nr. | Structure | HPLC (% B) | MS calculated (M + H)$^+$ found |
|---|---|---|---|
| 2 | 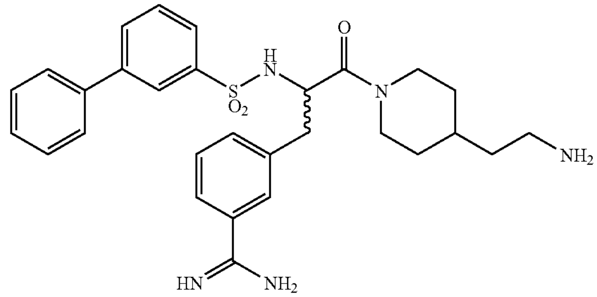 [SMILES: N=C(N)c1cccc(CC(NS(=O)(=O)c2cccc(-c3ccccc3)c2)C(=O)N2CCC(CCN)CC2)c1] | 31.92 | 533.25 534.4 |
| 3 | 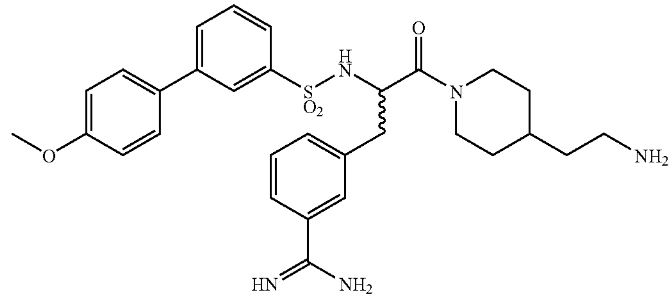 [SMILES: COc1ccc(-c2cccc(S(=O)(=O)NC(Cc3cccc(C(=N)N)c3)C(=O)N3CCC(CCN)CC3)c2)cc1] | 32.36 | 563.26 564.3 |
| 4 | 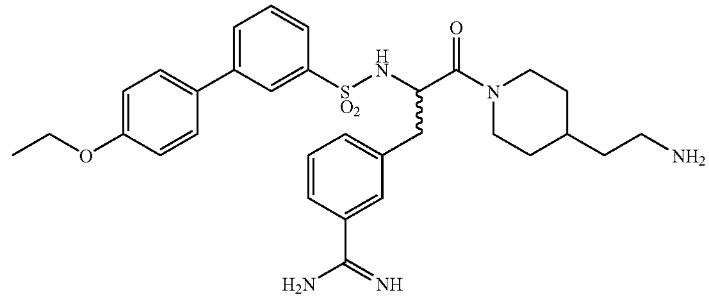 [SMILES: CCOc1ccc(-c2cccc(S(=O)(=O)NC(Cc3cccc(C(=N)N)c3)C(=O)N3CCC(CCN)CC3)c2)cc1] | 35.94 | 577.27 578.4 |

TABLE 1-continued

| Example/Nr. | Structure | HPLC (% B) | MS calculated (M + H)+ found |
|---|---|---|---|
| 5 | 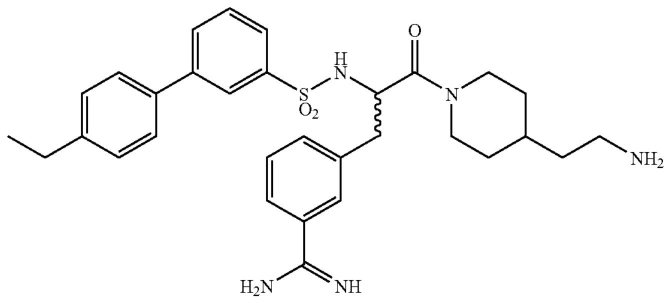 [SMILES: CCc1ccc(-c2cccc(S(=O)(=O)NC(Cc3cccc(C(=N)N)c3)C(=O)N3CCC(CCN)CC3)c2)cc1] | 37.89 | 561.28 562.3 |
| 6 | 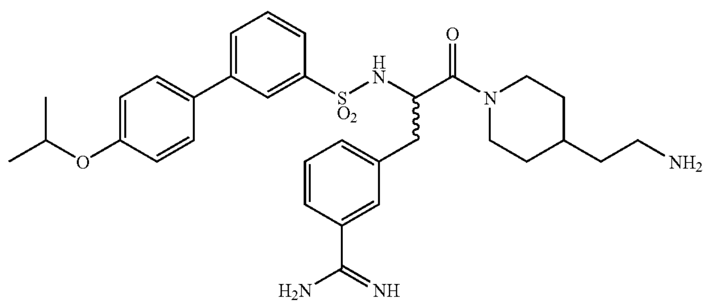 [SMILES: CC(C)Oc1ccc(-c2cccc(S(=O)(=O)NC(Cc3cccc(C(=N)N)c3)C(=O)N3CCC(CCN)CC3)c2)cc1] | 38.25 | 591.29 592.3 |
| 7[a] | 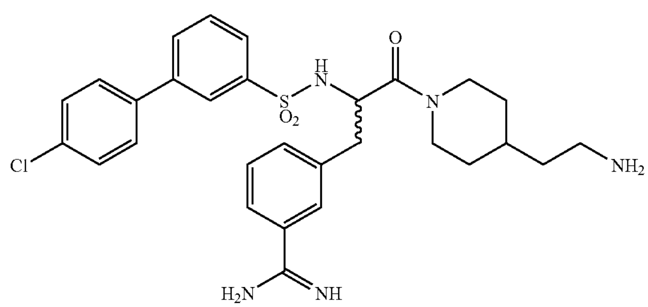 [SMILES: N=C(N)c1cccc(CC(NS(=O)(=O)c2cccc(-c3ccc(Cl)cc3)c2)C(=O)N2CCC(CCN)CC2)c1] | 35.46 | 567.21 568.3 |
| 8[a] | 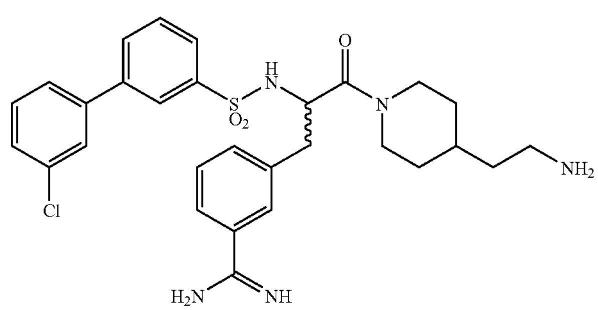 [SMILES: N=C(N)c1cccc(CC(NS(=O)(=O)c2cccc(-c3cccc(Cl)c3)c2)C(=O)N2CCC(CCN)CC2)c1] | 35.82 | 567.21 568.3 |
| 9[a] | 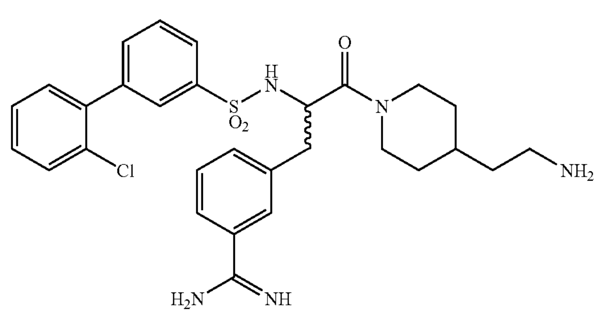 [SMILES: N=C(N)c1cccc(CC(NS(=O)(=O)c2cccc(-c3ccccc3Cl)c2)C(=O)N2CCC(CCN)CC2)c1] | 34.88 | 567.21 568.4 |

TABLE 1-continued

| Example/Nr. | Structure | HPLC (% B) | MS calculated (M + H)+ found |
|---|---|---|---|
| 10[b] | 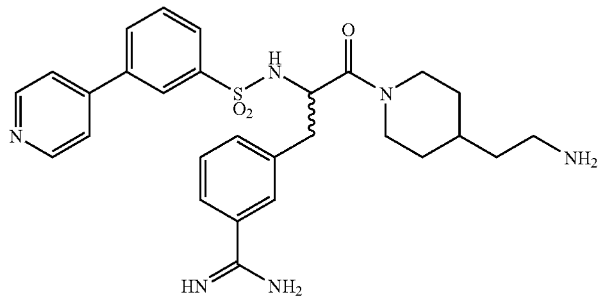 [SMILES: N=C(N)c1cccc(CC(NS(=O)(=O)c2cccc(-c3ccncc3)c2)C(=O)N2CCC(CCN)CC2)c1] | 19.3 | 534.24 535.3 |
| 11[b] | 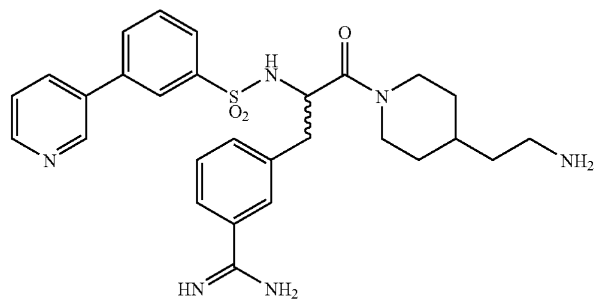 [SMILES: N=C(N)c1cccc(CC(NS(=O)(=O)c2cccc(-c3cccnc3)c2)C(=O)N2CCC(CCN)CC2)c1] | 19.1 | 534.24 535.6 |
| 12[c] | 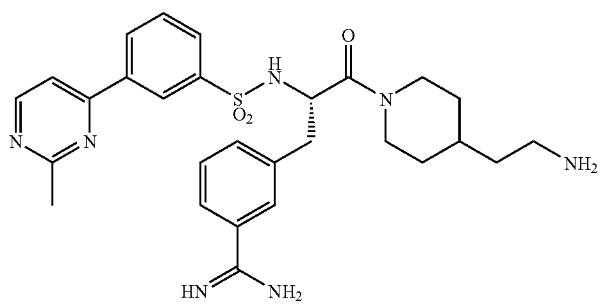 [SMILES: Cc1nccc(-c2cccc(S(=O)(=O)N[C@@H](Cc3cccc(C(=N)N)c3)C(=O)N3CCC(CCN)CC3)c2)n1] | 24.16 | 549.25 550.3 |
| 13 | 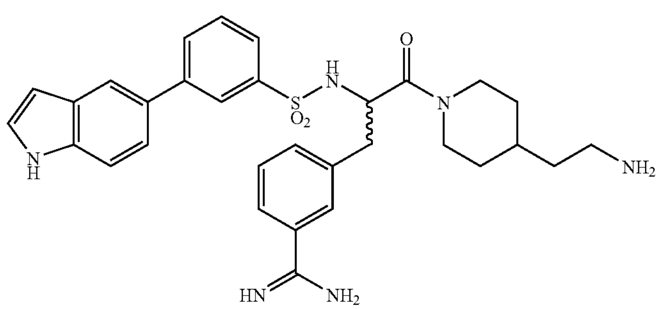 [SMILES: N=C(N)c1cccc(CC(NS(=O)(=O)c2cccc(-c3ccc4[nH]ccc4c3)c2)C(=O)N2CCC(CCN)CC2)c1] | 32.62 | 572.26 573.3 |
| 14[b,d] | 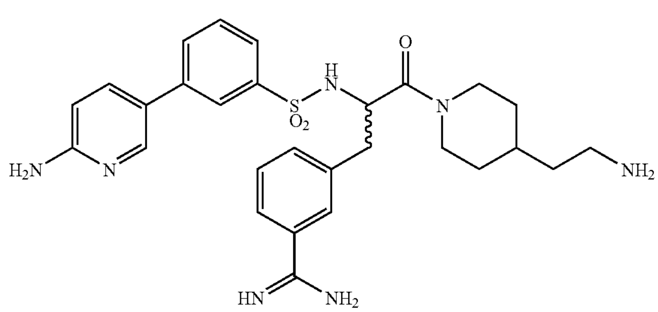 [SMILES: N=C(N)c1cccc(CC(NS(=O)(=O)c2cccc(-c3ccc(N)nc3)c2)C(=O)N2CCC(CCN)CC2)c1] | 20.4 | 549.25 550.3 |

TABLE 1-continued

| Example/Nr. | Structure | HPLC (% B) | MS calculated (M + H)+ found |
|---|---|---|---|
| 15[e] | 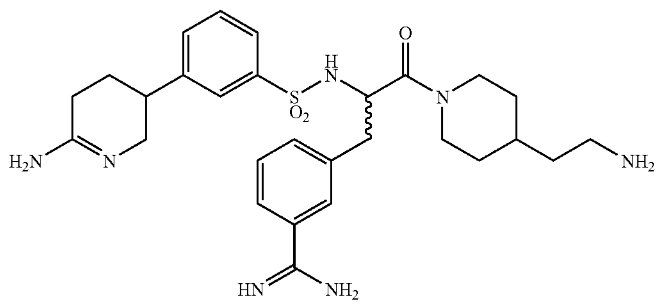 [SMILES: N=C(N)c1cccc(CC(NS(=O)(=O)c2cccc(C3CCC(N)=NC3)c2)C(=O)N2CCC(CCN)CC2)c1] | 19.6 | 553.28 554.4 |

[a] The amidino group of the inhibitors 7-9 was assembled through the reduction of the acetyl hydroxyamidin by zinc glacial acetate (Steinmetzer et al., J. Med. Chem. 49, 2006, 4116).
[b] The Suzuki coupling step c for the synthesis of these inhibitors was performed in a focused microwave synthesis "Discover" from the company CEM (t = 60-120 min, T = 100-120° C., 200-240 W).
[c] For the synthesis of these compounds, the commercially available 3-(2-methyl-4-pyrimidyl sulfonyl-Cl (Maybridge) was directly coupled at 3-1-cyanophenylalanine.
[d] For the synthesis of these compounds, 6-aminopyridine-3-boronic acid-pinacol ester (Aldrich) was used for the similar step c (see example 1), whereby the intermediate product obtained was replaced by Boc-pyrocarbonate. The following reaction steps were performed in a similar manner to the synthesis of inhibitor 1
[e] The compound was obtained through hydrogenation of the inhibitor 14 with Pd/C as catalyst under standard conditions (hydrogen, 1 bar).

Example 16

3-(1-aminobutyl)-phenyl sulfonyl-Phe(3-Amidino)-4-(2-amino ethyl)piperidide×3 TFA

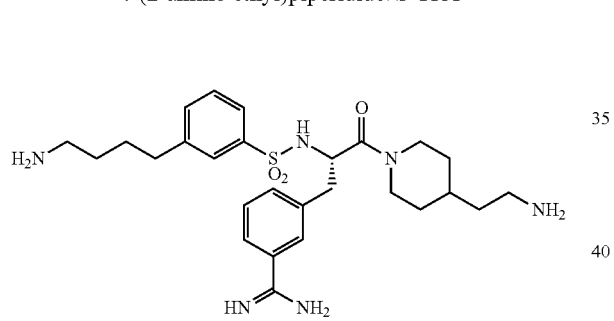

16a) 1-(Cbz-amino)-3-butene

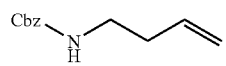

500 mg (7.03 mmol) 3-butene-1-amine (Aldrich) is suspended in 15 ml dioxane and treated with 7.1 ml 1 N NaOH. The clear solution is cooled down in an ice bath and mixed in portions with a total of 990 µl Cbz-Cl. The pH is set at 9-10 by adding additional NaOH solution. The reaction solution is stirred one hour at 0° C. and overnight at RT. The SV is removed u.V., the remainder removed with ethyl acetate and washed 2× with saturated NaCl solution. The solvent is dried with $Na_2SO_4$ and removed u.V.

Yield: 980 mg colorless oil

DC: (4/1/1 n-butanol/glacial acetic acid/water): $R_f$=0.86

16b) 3-iod phenyl sulfonyl-Phe(3-CN)—OH

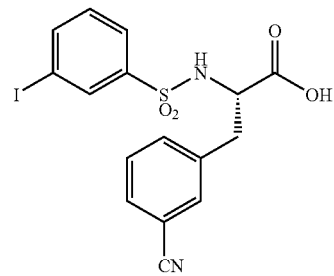 [SMILES: N#Cc1cccc(C[C@H](NS(=O)(=O)c2cccc(I)c2)C(=O)O)c1]

0.76 g (4 mmol) H-Phe(3-CN)—OH (Senn Chemicals AG, Dielsdorf, Switzerland) are suspended in 20 ml water and 4 ml dioxane and dissolved by adding 765 µl (4.4 mmol) DIEA. Under ice cooling, a solution of 1.33 g (4.4 mmol) 3-iod phenyl-sulfonyl chloride (produced similarly to Langmuir, Chem. Berichte 28, 90-96, 1895) is dissolved in ca. 15 ml dioxane, added dropwise within 30 min. The pH is evaluated and set at 8-9 through addition of DIEA (a total of 830 µl in several portions) It is stirred for 30 min further at 0° C. and 4 h at RT. The solvent is removed through a vacuum and the remainder is dissolved in water through addition of 1 N NaOH (pH ca. 10). The aqueous phase is extracted once with ethyl acetate and acidified with 6 N HCl (pH ca. 2). The aqueous phase is extracted 3 times with ethyl acetate. Subsequently, the ethyl acetate is washed 3 times with saturated NaCl solution, the SV dried with $Na_2SO_4$ and removed through a vacuum.

Yield: 1.7 g (3.72 mmol) weak yellowish solid

HPLC: 50.28% B 16c) 3-iod phenyl sulfonyl-Phe(3-CN)-4-(2-Boc-amidoethyl)piperidide

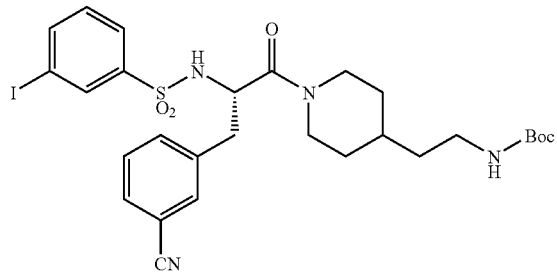 [SMILES: CC(C)(C)OC(=O)NCCC1CCN(C(=O)[C@H](Cc2cccc(C#N)c2)NS(=O)(=O)c2cccc(I)c2)CC1]

1.14 g (2.5 mmol) 3-iod phenyl sulfonyl-d/l-Phe(3-CN)—OH and 570 mg (2.5 mmol) 4-(2-Boc-amidoethyl)piperidide (Steinmetzer et al., J. Med. Chem. 49, 2006, 4116) is dissolved in 8 ml DMF by adding 0.87 ml (5 mmol) DIEA and mixed at 0° C. with 1.3 g (2.5 mmol) PyBop. The reaction solution is stirred for 30 min at 0° C. and 4 h at RT and the SV is removed through a vacuum. The remainder is extracted in EE and washed 3 times with 5% $KHSO_4$-solution, 1 time with saturated NaCl solution, 3 times with saturated $NaHCO_3$-solution and 3 times with saturated NaCl solution. The SV is dried with $Na_2SO_4$ and removed through a vacuum. The residual remainder is purified using preparative HPLC and the solvent is removed u.V.

Yield: 1.1 g lyophilized powder

HPLC: 65.17% B 16d) 3-(Cbz-NH—$(CH_2)_2$—CH=CH)-phenyl sulfonyl-Phe(3-CN)-4-(2-Boc-amidoethyl)-piperidide

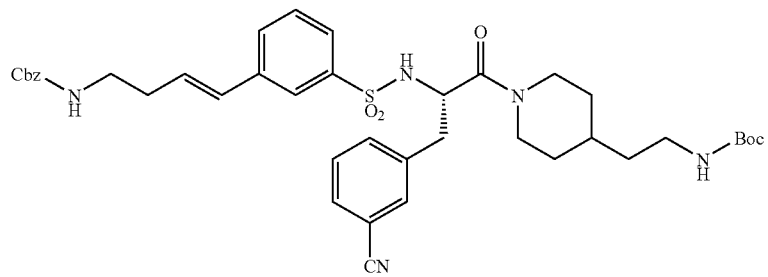 [SMILES: CC(C)(C)OC(=O)NCCC1CCN(C(=O)[C@H](Cc2cccc(C#N)c2)NS(=O)(=O)c2cccc(/C=C/CCNC(=O)OCc3ccccc3)c2)CC1]

170 mg (0.255 mmol) 3-iod phenyl sulfonyl-d/l-Phe(3-CN)-4-(2-Boc-amidoethyl)piperidide, 5 mg Pd-(II)-acetate and 65 mg (0.771 mmol) $NaHCO_3$ are treated with 3 ml DMF and 2 ml water. The reaction solution is heated to 50° C., treated with 68 mg (0.244 mmol) tetrabutylammonium chloride and 58 mg (0.28 mmol) Cbz-NH—$(CH_2)_2$—CH=$CH_2$ and stirred overnight at 50° C. The solvent is removed u.V., the remainder is dissolved in 50% acetonitrile and the pH is set at 4 by adding acetic acid. The product is purified using preparative HPLC and the solvent of the fractions containing the product is removed u.V.

Yield: 65 mg oil, HPLC: 67.44 and 67.92% in a 3:1 ratio

MS: ber. 743.34 gef. 766.5 $(M+Na)^+$ 16e) 3-(Cbz-NH—$(CH_2)_4$)-phenyl sulfonyl-Phe(3-CN)-4-(2-Boc-amidoethyl)piperidide

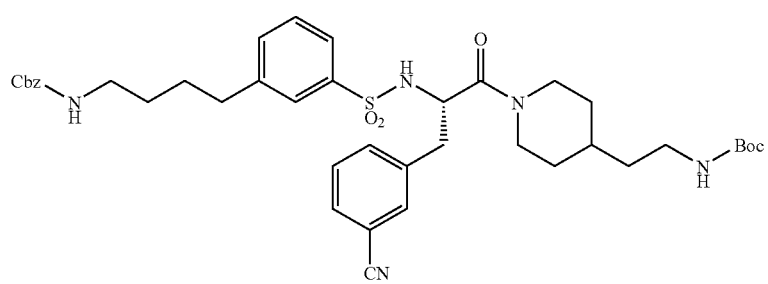 [SMILES: CC(C)(C)OC(=O)NCCC1CCN(C(=O)[C@H](Cc2cccc(C#N)c2)NS(=O)(=O)c2cccc(CCCCNC(=O)OCc3ccccc3)c2)CC1]

65 mg of the oily 3-(Cbz-NH—(CH$_2$)$_2$—CH═CH)-phenyl sulfonyl-Phe(3-CN)-4-(2-Boc-amidoethyl)piperidide is dissolved in 50 ml ethyl acetate, treated with a small quantity of Pd/C catalyst and hydrogenated overnight with hydrogen. The catalyst is filtered out and the SV removed u.V.

Yield: 45 mg colorless oil,

HPLC: 68.28%, MS: ber. 745.34 gef. 768.5 (M+Na)$^+$ 16f) 3-(Cbz-NH—(CH$_2$)$_4$)-phenyl sulfonyl-Phe(3-acetyl-hydroxyamidino)-4-(2-Boc-amido-ethyl)piperidide

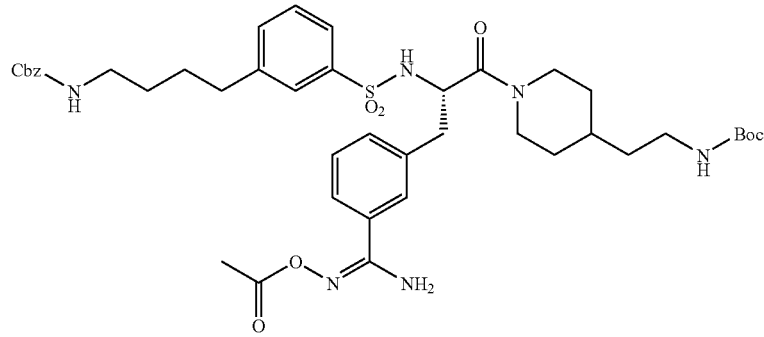 [SMILES: CC(=O)O/N=C(/N)c1cccc(C[C@H](NS(=O)(=O)c2cccc(CCCCNC(=O)OCc3ccccc3)c2)C(=O)N2CCC(CCNC(=O)OC(C)(C)C)CC2)c1]

44 mg (ca. 0.06 mmol) 3-(Cbz-NH—(CH$_2$)$_4$)-phenyl sulfonyl-Phe(3-CN)-4-(2-Boc-amidoethyl)piperidide are dissolved in 2 ml ethanol and treated with 17 mg (0.24 mmol) hydroxylamine×HCl and 42 µl (0.24 mmol) DIEA. The reaction solution is heated for 6 h under flow back and stirred overnight at RT. The solvent is removed u.V., the remainder (HPLC: 51.78% B) is dissolved in 2 ml acetic acid and treated with 47 µl (0.5 mmol) acetic acid anhydride. The reaction solution is stirred for 30 min and the solvent removed u.V. The raw product (HPLC: 62.6% B) is used unmixed for the next reaction step.

16) 3-(1-aminobutyl)-phenyl sulfonyl-Phe(3-Amidino)-4-(2-amino ethyl)piperidide×3 TFA

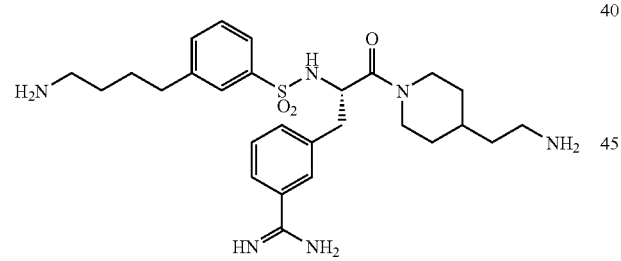

The raw product in 3-(Cbz-NH—(CH$_2$)$_4$)-phenyl sulfonyl-Phe(3-acetyl-hydroxyamidino)-4-(2-Boc-amidoethyl)piperidide is dissolved in 10 ml 90% acetic acid and hydrogenated overnight with Pd/C as catalyst and hydrogen. The catalyst is filtered out, the filtrate is compressed u.V. and the remainder (HPLC: 33.76% B) is treated with 2 ml TFA. The reaction solution is shaken for an hour, the solvent compressed as much as possible u.V., and the product is purified and lyophilized with preparative HPLC.

Yield: 15 mg lyophilized powder

HPLC: 19.48%, MS: ber. 528.29 gef. 529.29 (M+H)$^+$

Example 17

N-(3-β-Ala)amidophenyl sulfonyl-Phe(3-Am)-piperidine buteryl-N-methylamide×2 TFA

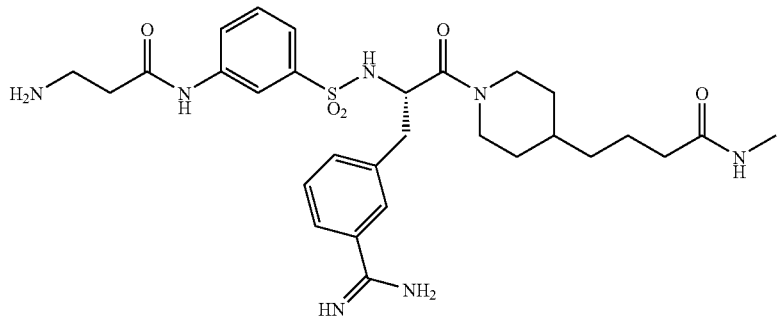

17a) H-Phe(3-CN)—OMe×HCl

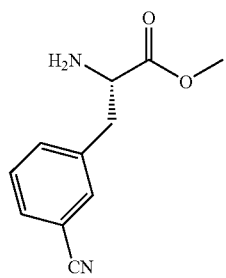

945 mg (4.97 mmol) H-Phe(3-CN)—OH are suspended in 4 ml methanol and mixed dropwise with 500 µl (6.87 mmol) thionyl chloride at −15° C. After ca. 1/3 of the thionyl chloride is added, the amino acids will disengage and each partial product precipitates after the addition is completed. The reaction solution is stirred for 30 min further at −15° C. and then slowly warmed up to RT. The reaction solution is stirred for 5 h further at RT, whereby all is dissolved. The solvent is compressed as much as possible u.V. and the product precipitated by adding ether, extracted and washed with ether.

Yield: 1.19 g (4.94 mmol) white solid

HPLC: 20.53% B

17b) 3-NO$_2$-phenyl sulfonyl-Phe(3-CN)—OMe

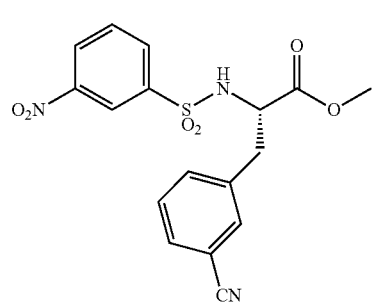 [SMILES: COC(=O)[C@H](Cc1cccc(C#N)c1)NS(=O)(=O)c1cccc([N+](=O)[O-])c1]

580 mg (2.4 mmol) H-Phe(3-CN)—OMe×HCl are dissolved in 2 ml DMF by adding 418 µl (2.4 mmol) DIEA. 560 mg (2.52 mmol) 3-NO$_2$-phenyl sulfonyl-chloride are added in several portions at 0° C., the pH is set to 8-9 with more DIEA. The reaction solution is stirred for 1 h at 0° C. and overnight at RT. The solvent is removed u.V. and the remainder dissolved in ethyl acetate, and washed 3 times with 5% KHSO$_4$-solution, once with saturated NaCl solution, 3 times with saturated NaHCO$_3$-solution and 3 times with saturated NaCl solution. The SV is dried with Na$_2$SO$_4$ and removed u.V.

Yield: 580 mg (1.488 mmol) yellow oil

HPLC: 52.45% B

17c) 3-NH$_2$-phenyl sulfonyl-Phe(3-CN)—OMe

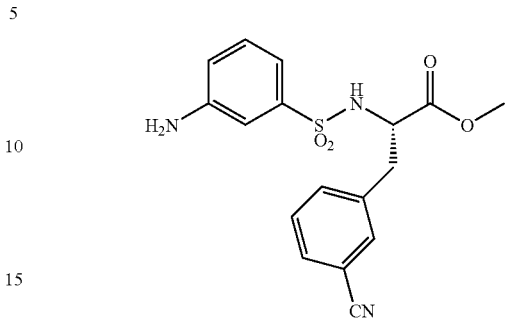

580 mg 3-NO$_2$-phenyl sulfonyl-Phe(3-CN)—Ome are dissolved in 15 ml 90% acetic acid and treated with zinc dust. The reaction solution is stirred for 2 h at RT, the remaining residue on zinc dust is filtered out and the solvent is removed u.V. The remainder is incorporated with ethyl acetate, and washed twice with saturated NaHCO$_3$-solution and twice with saturated NaCl solution. The SV is dried with Na$_2$SO$_4$ and removed through a vacuum.

Yield: 405 mg (1.12 mmol) yellow oil

HPLC: 39.75% B

17d) Cbz-βAla-3-NH-phenyl sulfonyl-Phe(3-CN)—OMe

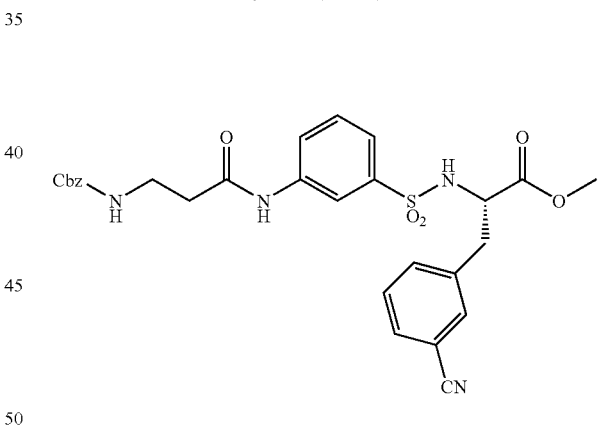

200 mg (0.90 mmol) Cbz-β-Ala-OH are dissolved in 4 ml DMF, treated with 100 µl NMM (0.90 mmol) and cooled down to −15° C. 117 µl CKIBE (0.90 mmol) is added and the reaction solution stirred 10 min further at −15° C. Then 380 mg (1.06 mmol) 3-NH$_2$-phenyl sulfonyl-Phe(3-CN)—OMe and 50 µl NMM (0.45 mmol) are added and the reaction solution is stirred for 1 h at −15° C. and overnight at RT. The SV is removed u.V., the remainder incorporated with ethyl acetate and washed 3 times with 5% KHSO$_4$-solution, once with saturated NaCl solution, 3 times with saturated NaHCO$_3$-solution and 3 times with saturated NaCl solution. The SV is dried with Na$_2$SO$_4$ and removed through a vacuum.

Yield: 460 mg (0.81 mmol) yellow oil

HPLC: 54.15% B, MS ber.: 564.17 gef.: 563.0 (M−H)$^-$

17e) Cbz-βAla-3-NH-phenyl sulfonyl-Phe(3-CN)—OH

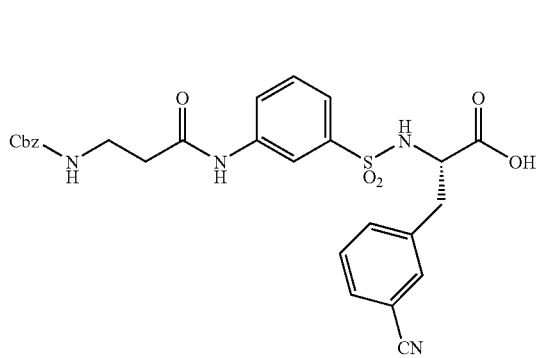 [SMILES: N#Cc1cccc(C[C@H](NS(=O)(=O)c2cccc(NC(=O)CCNC(=O)OCc3ccccc3)c2)C(=O)O)c1]

455 mg (0.806 mmol) Cbz-βAla-3-NH-phenyl sulfonyl-Phe(3-CN)—Ome are dissolved in 2 ml dioxane and treated with 2 ml 1 N LiOH. The homogenous solution is stirred for 2 h at RT and then neutralized with 2 ml 1 N HCl. The SV is removed u.V., the remainder incorporated with ethyl acetate and washed 3 times with 5% $KHSO_4$-solution and 3 times with saturated saline solution. The organic phase is dried with $Na_2SO_4$ and compressed under vacuum.

Yield: 390 mg foam

HPLC: 48.99% B, MS ber.: 550.15; gef.: 549.0 $(M-H)^-$.

17f) Cbz-βAla-3-NH-phenyl sulfonyl-Phe(3-OxAm)-OH

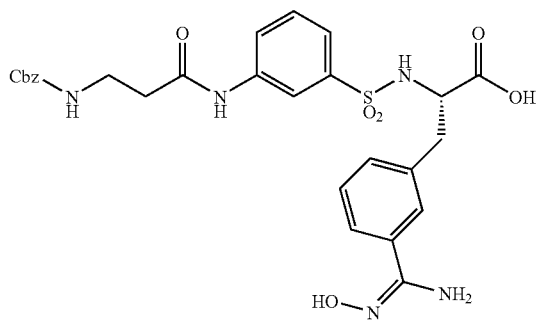 [SMILES: N/C(=N/O)c1cccc(C[C@H](NS(=O)(=O)c2cccc(NC(=O)CCNC(=O)OCc3ccccc3)c2)C(=O)O)c1]

390 mg (0.71 mmol) Cbz-βAla-3-NH-phenyl sulfonyl-Phe (3-CN)—OH are dissolved in 5 ml abs. ethanol, treated with 73 mg (1.05 mmol) hydroxylaminhydrochloride and 184 µl (1.05 mmol) DIEA and cooked for 4 h under back flow. It is stirred further overnight at RT. The solvent is removed u.V. and the residual remainder purified by means of preparative HPLC and the product lyophilized.

Yield: 202 mg lyophilized powder

HPLC: 35.68% B

17g) Cbz-βAla-3-NH-phenyl sulfonyl-Phe(3-AcOxAm)-OH

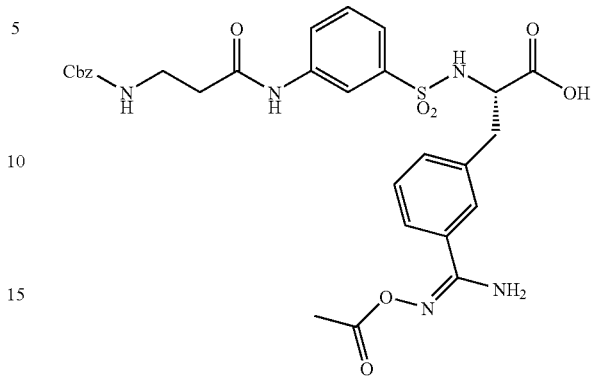

202 mg Cbz-βAla-3-NH-phenyl sulfonyl-Phe(3-OxAm)-OH are dissolved in glacial acetic acid, treated with 143 µl (1.5 mmol) acetanhydride and stirred for one hour at room temperature. The solvent is removed through a vacuum and the remainder is lyophilized from tert-butanol.

Yield: 240 mg lyophilized powder

HPLC: 44.95% B

17h) Cbz-4-piperidine butyric acid

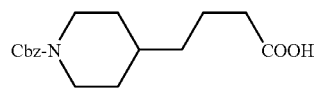

3.984 g (19.18 mmol) 4-piperidine butyric acid×HCl are dissolved in 15 ml water and 40 ml 1 N NaOH, and mixed dropwise under ice cooling with 3.3 ml (23.2 mmol) Cbz-C previously dissolved in 5 ml dioxane. The pH is determined and kept constant at 9-10. The reaction solution is stirred for one more hour at 0° C. and overnight at RT. The SV is removed u.V., the remainder dissolved in basic water and 2× extracted with ethyl acetate. The aqueous phase is acidulated through the addition of HCl and extracted 3× with ethyl acetate. The ethyl acetate phase is washed 3× with saturated NaCl solution, dried with $Na_2SO_4$ and the SV is compressed u.V.

Yield: 5.6 g colorless oil, MS ber.: 305.16; gef.: 304.2 $(M-H)^-$.

HPLC: 51.84% B

17i) Cbz-4-piperidine buteryl-N-methyl amide

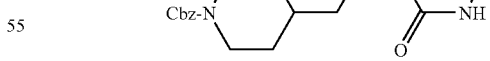

570 mg (ca. 1.86 mmol) Cbz-4-piperidine butyric acid were dissolved in 7 ml DMF and mixed at 0° C. with 135 mg (2 mmol) methylamine×HCl, 968 mg (1.86 mmol) PyBop and 647 µl (3.72 mmol) DIEA. The reaction solution was stirred for 30 min under ice cooling and 3 h further at RT. The SV is removed u.V. and the product is purified using preparative HPLC and lyophilized from 80% tert-butanol.

Yield: 230 g colorless oil, MS ber.: 318.19; gef.: 319.2 $(M+H)^+$.

HPLC: 47.51% B

17j) H-piperidine buteryl-N-methyl amide×HBr

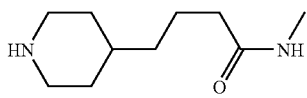

150 mg of the oily Cbz-4-piperidine buteryl-N-methyl amide are treated with 1 ml 35% HBr in glacial acetic acid. The reaction solution is left for 1 h at RT and then treated with ether. The product will separate at the brim of the flask in oily form, the supernatant is decanted and the remainder dissolved in methanol and once again precipitated with ether. The supernatant is decanted again and the remainder dried under vacuum.

Yield: 129 mg white solid

17k) Cbz-βAla-3-NH-phenyl sulfonyl-Phe(3-AcOxAm)-piperidine buteryl-N-methyl amide

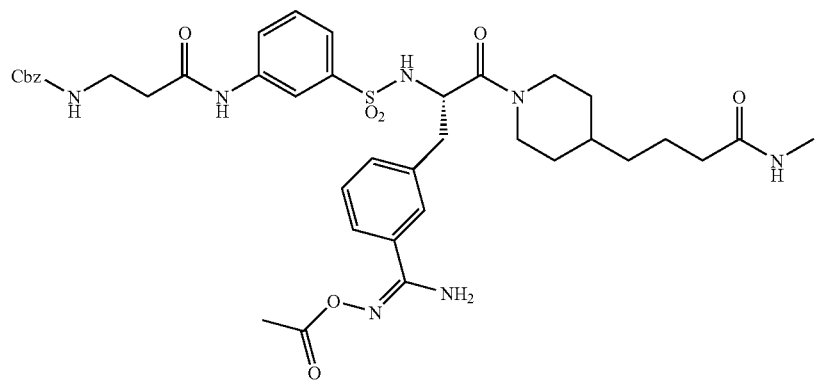 [SMILES: CNC(=O)CCCC1CCN(C(=O)[C@H](Cc2cccc(/C(N)=N\OC(C)=O)c2)NS(=O)(=O)c2cccc(NC(=O)CCNC(=O)OCc3ccccc3)c2)CC1]

34.5 mg (0.055 mmol) Cbz-βAla-3-NH-phenyl sulfonyl-Phe(3-AcOxAm)-OH and 14.9 mg (0.056 mmol) piperidine buteryl-N-methyl amide×HBr are dissolved in 1.5 ml DMF and mixed at 0° C. with 29 mg (0.055 mmol) PyBop and 19.2 µl (0.11 mmol) DIEA. The reaction solution is stirred for 30 minutes at 0° C. and 2 h at room temperature and the solvent is removed u.V. The remainder is removed in ethyl acetate and washed 3× with 5% KHSO$_4$-solution, 1× with saturated saline solution, 3× with saturated NaHCO$_3$-solution and 3× with saturated saline solution. The organic phase is dried with Na$_2$SO$_4$ and compressed under vacuum.

Yield: 46 mg oil, MS ber.: 791.33; gef.: 790.1 [M−H]⁻ and 814.5 [M+Na]⁺.

HPLC: 45.95% B

17) H-βAla-3-NH-phenyl sulfonyl-Phe(3-Am)-piperidine buteryl-N-methyl amide×2 TFA

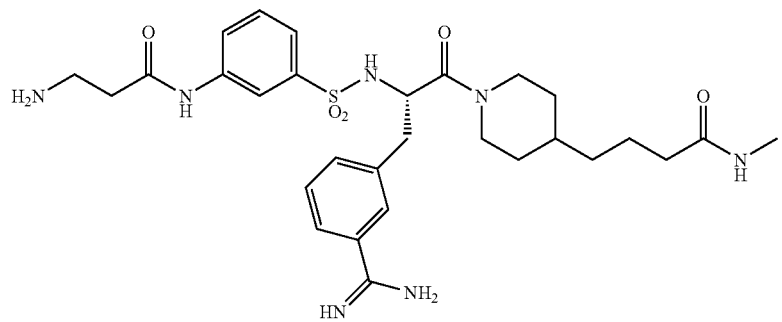 [SMILES: CNC(=O)CCCC1CCN(C(=O)[C@H](Cc2cccc(C(=N)N)c2)NS(=O)(=O)c2cccc(NC(=O)CCN)c2)CC1]

46 mg of oily raw product in Cbz-βAla-3-NH-phenyl sulfonyl-Phe(3-AcOxAm)-piperidine buteryl-N-methyl amide are dissolved in 50 ml acetic acid (90%), treated with 5 mg catalyst (10% Pd/C) and hydrogenated for 64 hours at room temperature with hydrogen. The catalyst is filtered out, the SV compressed u.V. and the remainder purified by means of preparative HPLC and the product lyophilized.

Yield: 24 mg lyophilized powder, MS ber.: 599.29; gef.: 600.4 [M+H]⁺,

HPLC: 23.72% B

Further compounds with a C-terminal piperidine butyric acid-methyl amide, methyl ester, amide and free acid function were produced similarly to the described synthesis instructions for the inhibitors 1 and 17 (table 2). 4-piperidyl butyric acid methyl ester, necessary precursor for inhibitor 20, was produced by exchanging the 4-piperidyl butyric acid with thionyl chloride in methanol; the corresponding amide for inhibitor 21 was produced by exchanging the methyl ester with 7 N ammoniac in methanol (reaction duration: 4 days). The inhibitor 22 with a free C-terminal acid function was synthesized through a final saponification of the inhibitor 20 with LiOH solution.

The inhibitors 23-27a were produced similarly to the synthesis instructions of inhibitor 17, whereas H-iNip-NH$_2$ (inhibitor 23), H-Nip-NH$_2$ (inhibitor 24), H-Pzd-COOEt (inhibitor 25), H-Pzd-Cbz (inhibitors 26 and 27) and piperidine (inhibitor 27a) were used as amine components similarly to step 17k. For the inhibitors 26 and 27, Boc-β-Ala-OH was used as a carboxyl component instead of Cbz-β-Ala-OH in the similar step 17d, the separation of the Boc group was attained in the final step by adding 90% TFA. In the case of inhibitor 26, the amidine was produced through reduction of the acetyl hydroxyamidino group using zinc dust in AcOH. For the synthesis of inhibitors 27b-27d, lactam pyridazinone (for 27b), piperidinone (for 27c) and Cbz-piperazinone (for 27d) were prepared, whereby the amidation of the aryl halide 3-iodophenyl sulfonyl-3-cyanophenylalanine-4-(methylamido buteryl)piperidide was carried out by means of the copper-catalyzed reaction using known methods (addition of ca. 1 mol % CuI, ca. 2 equivalents to $K_3PO_4$, ca. 10 mol % (1R,2R)—N,N'-dimethyl-1,2-cyclohexanediamine in DMF at 110° C., ca. 2 h, Klappars et al., J. Am. Chem. Soc. 2001, 123, 7727-7729).

Examples 18-29

The pro-drugs with free hydroxyamidino function were produced from the compounds 18 and 19 (inhibitors 28 and 29).

TABLE 2

| Example/Nr. | Structure | HPLC (% B) | MS calculated $(M + H)^+$ found |
|---|---|---|---|
| 18 | 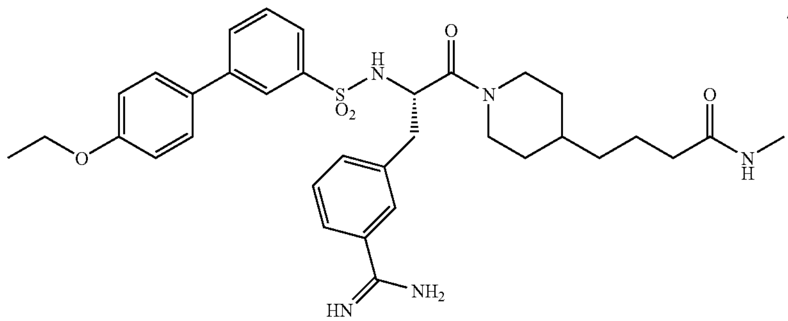 [SMILES: CCOc1ccc(-c2cccc(S(=O)(=O)N[C@@H](Cc3cccc(C(=N)N)c3)C(=O)N3CCC(CCCC(=O)NC)CC3)c2)cc1] | 43.93 | 633.3 634.3 |
| 19 | 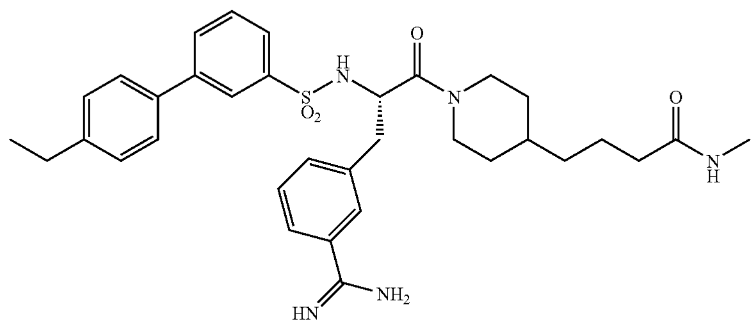 [SMILES: CCc1ccc(-c2cccc(S(=O)(=O)N[C@@H](Cc3cccc(C(=N)N)c3)C(=O)N3CCC(CCCC(=O)NC)CC3)c2)cc1] | 48.31 | 617.3 618.2 |
| 20 | 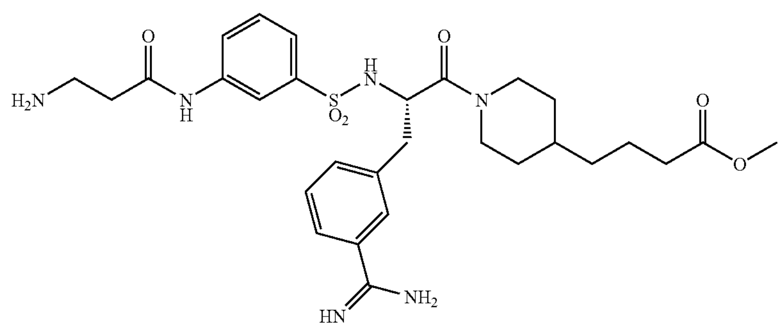 [SMILES: COC(=O)CCCC1CCN(C(=O)[C@H](Cc2cccc(C(=N)N)c2)NS(=O)(=O)c2cccc(NC(=O)CCN)c2)CC1] | 29.60 | 600.27 601.3 |
| 21 | 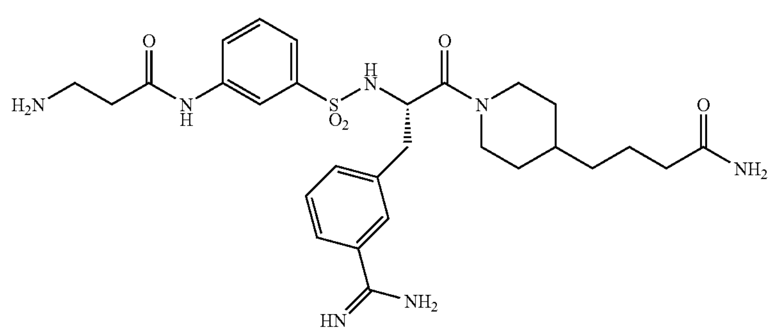 [SMILES: N=C(N)c1cccc(C[C@H](NS(=O)(=O)c2cccc(NC(=O)CCN)c2)C(=O)N2CCC(CCCC(N)=O)CC2)c1] | 22.60 | 585.27 586.3 |

TABLE 2-continued

| Example/Nr. | Structure | HPLC (% B) | MS calculated (M + H)+ found |
|---|---|---|---|
| 22 | 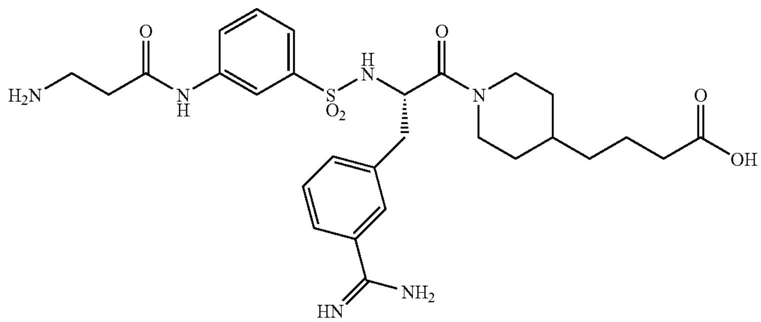 [SMILES: N=C(N)c1cccc(C[C@H](NS(=O)(=O)c2cccc(NC(=O)CCN)c2)C(=O)N2CCC(CCCC(=O)O)CC2)c1] | 25.8 | 586.26 587.3 |
| 23 | 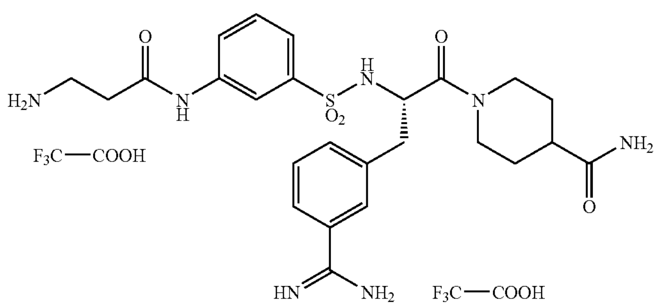 | 18.8 | 543.23 544.3 |
| 24 | 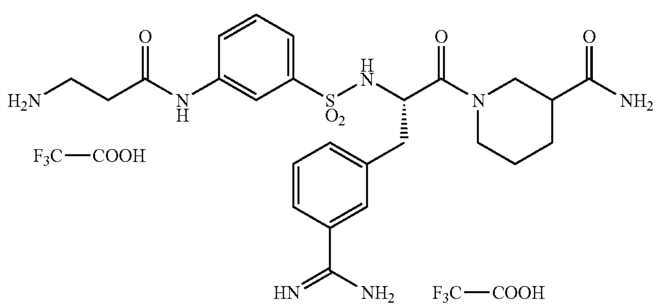 | 19.5 | 543.23 544.3 |
| 25 | 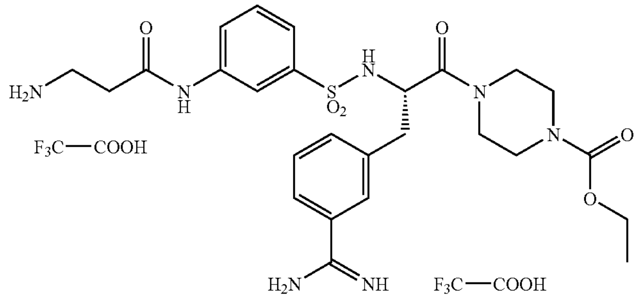 | 25.0 | 573.24 |

TABLE 2-continued

| Example/Nr. | Structure | HPLC (% B) | MS calculated (M + H)+ found |
|---|---|---|---|
| 26 | 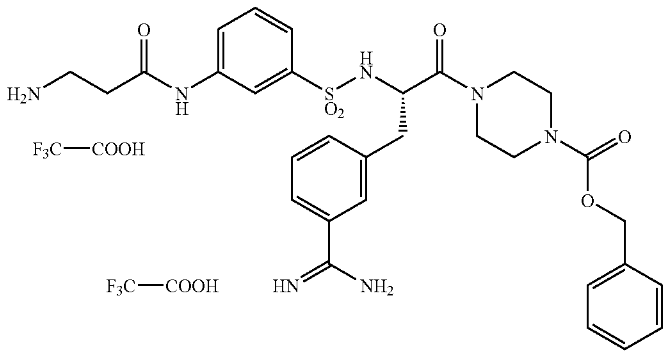 | 32.6 | 635.26 636.3 |
| 27 | 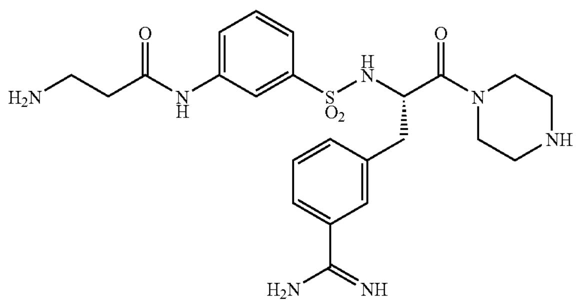 [SMILES: N=C(N)c1cccc(C[C@H](NS(=O)(=O)c2cccc(NC(=O)CCN)c2)C(=O)N2CCNCC2)c1] | 15.7 | 501.22 502.3 |
| 28 | 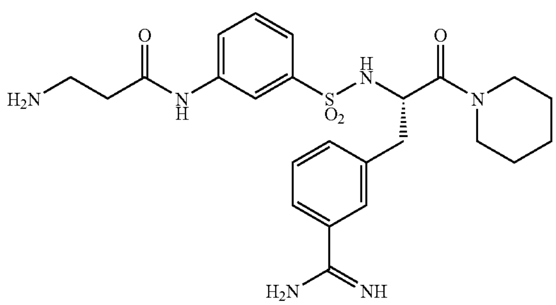 [SMILES: N=C(N)c1cccc(C[C@H](NS(=O)(=O)c2cccc(NC(=O)CCN)c2)C(=O)N2CCCCC2)c1] | 23.6 | 500.22 501.3 |
| 29 | 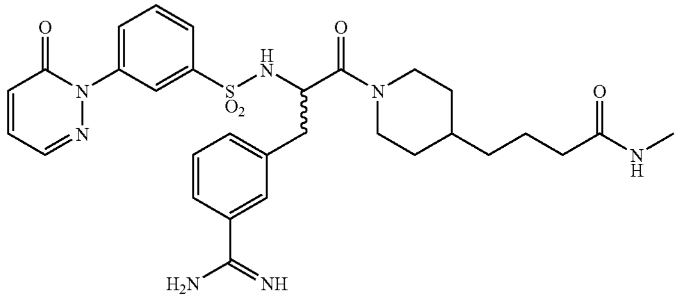 [SMILES: CNC(=O)CCCC1CCN(C(=O)C(Cc2cccc(C(=N)N)c2)NS(=O)(=O)c2cccc(-n3ncccc3=O)c2)CC1] | 31.78 | 607.26 608.2 |

TABLE 2-continued

| Example/Nr. | Structure | HPLC (% B) | MS calculated (M + H)+ found |
|---|---|---|---|
| 30 | 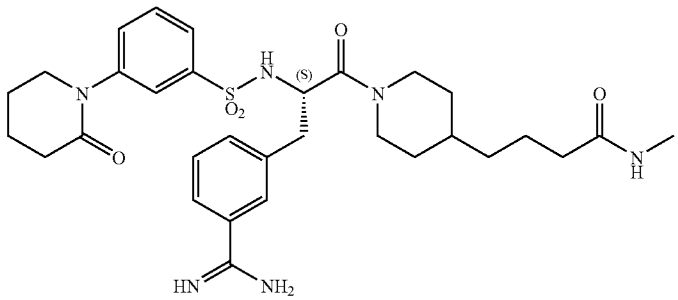 | 31.29 | 610.29 611.3 |
| 31 | 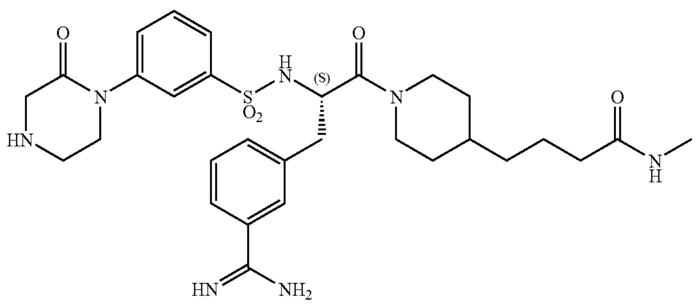 | 24.2 | 611.29 613.3 |
| Pro-drugs | | | |
| 32 | 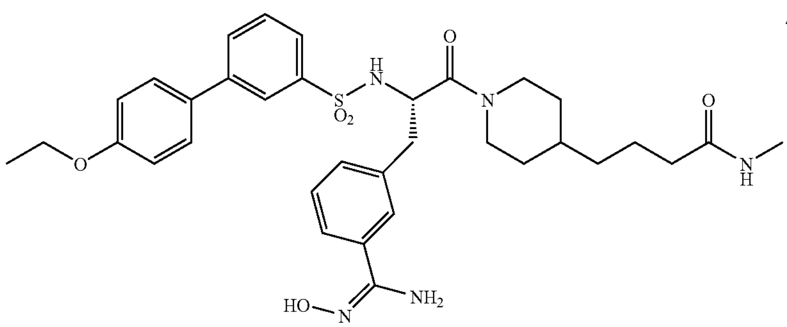 [SMILES: CCOc1ccc(-c2cccc(S(=O)(=O)N[C@@H](Cc3cccc(/C(N)=N\O)c3)C(=O)N3CCC(CCCC(=O)NC)CC3)c2)cc1] | 42.97 | 649.29 650.4 |
| 33 | 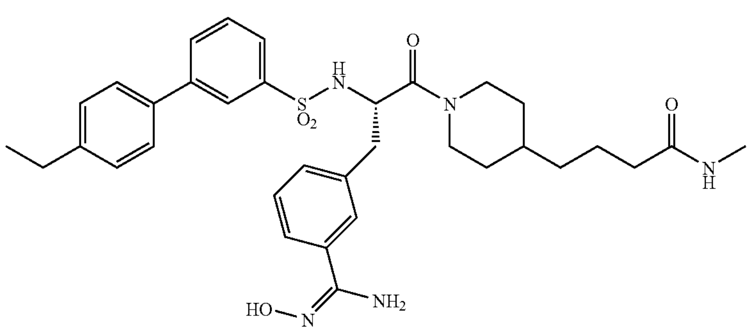 [SMILES: CCc1ccc(-c2cccc(S(=O)(=O)N[C@@H](Cc3cccc(/C(N)=N\O)c3)C(=O)N3CCC(CCCC(=O)NC)CC3)c2)cc1] | 47.49 | 633.3 634.3 |

Example 34

H-βAla-3-NH-phenyl sulfonyl-Phe(3-Ame)-(2-amino ethyl)piperidide×3 TFA

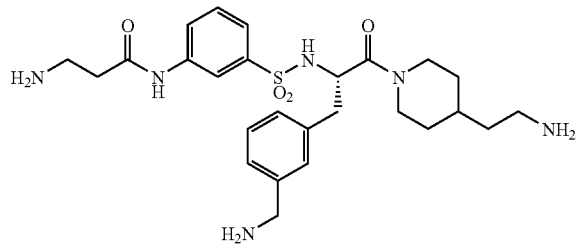 [SMILES: NCCC(=O)Nc1cccc(S(=O)(=O)N[C@@H](Cc2cccc(CN)c2)C(=O)N2CCC(CCN)CC2)c1]

34a)

3-NH$_2$-Phenyl sulfonyl-Phe(3-Ame)-OH×2 HCl

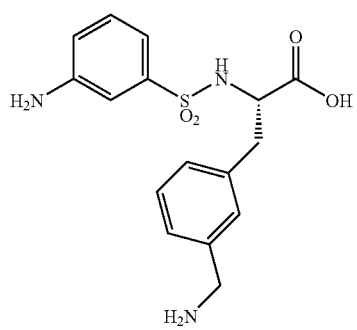 [SMILES: NCc1cccc(C[C@H](NS(=O)(=O)c2cccc(N)c2)C(=O)O)c1]

160 mg (0.425 mmol) 3-NO$_2$-phenyl sulfonyl-Phe(3-CN)—OH(HPLC: 45.49% B, Steinmetzer et al., J. Med. Chem. 49, 2006, 4116) were dissolved in 50 ml 90% acetic acid and 2 ml 1 N HCl and hydrogenated under normal pressure for 48 h with hydrogen and Pd/C as a catalyst. The solvent is removed u.V., the remainder dissolved in methanol and precipitated through addition of diethyl ether.

Yield: 133 mg powder, MS ber.: 349.11; gef.: 350.1 [M+H]$^+$,
HPLC: 19.5% B

34b)

3-NH$_2$-phenyl sulfonyl-Phe(3-Boc-Ame)-OH

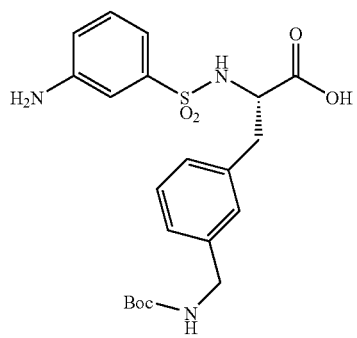 [SMILES: CC(C)(C)OC(=O)NCc1cccc(C[C@H](NS(=O)(=O)c2cccc(N)c2)C(=O)O)c1]

124 mg (0.294 mmol) 3-NH$_2$-phenyl sulfonyl Phe(3-Ame)-OH×2HCl were dissolved in 2 ml dioxane and 2 ml water through the addition of 102 µl (0.59 mmol) DIEA. 70 mg (0.32 mmol) Boc-pyrocarbonate, already dissolved in 500 µl dioxane, are divided into several portions at 0° C., whereby the pH is determined and set at 8.5-9 with DIEA. The reaction solution is stirred for 15 min further at 0° C. and overnight at RT. The SV is removed u.V., the remainder precipitated in ethyl acetate, washed 2× in NaCl-saturated water, dried with Na$_2$SO$_4$ and the SV compressed u.V.

Yield: 125 mg yellow oil, MS ber.: 449.1; gef.: 448.1 [M−H]$^-$,
HPLC: 41.6% B

34c)

3-NH$_2$-phenyl sulfonyl-Phe(3-Boc-Ame)-4-(2-Boc-amidoethyl)piperidide

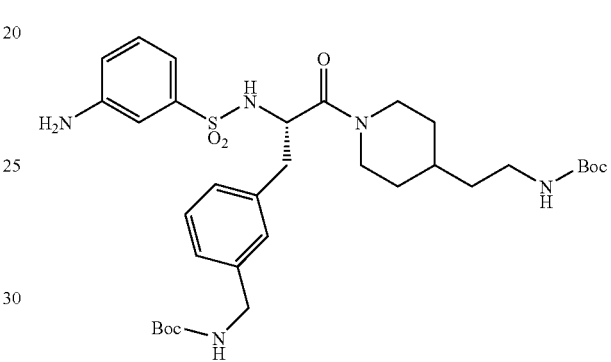

120 mg (0.267 mmol) 3-NH$_2$-phenyl sulfonyl-Phe(3-Boc-Ame)-OH and 64 mg (0.28 mmol) (2-Boc-amidoethyl)piperidine are dissolved in 4 ml DMF and treated with 138 mg (0.267 mmol) PyBop and 93 µl (0.534 mmol) DIEA at 0° C. The reaction solution is stirred for 30 min at 0° C. and overnight at RT. The SV is removed u.V., the remainder precipitated in ethyl acetate, and washed 2× in saturated NaHCO$_3$-solution, and 2× saturated saline solution. The organic phase is dried with Na$_2$SO$_4$ and compressed under vacuum.

Yield: 210 mg yellowish brown oil
HPLC: 57.38% B

34) H-βAla-3-NH-phenyl sulfonyl-Phe(3-Ame)-(2-amino ethyl)piperidide×3 TFA

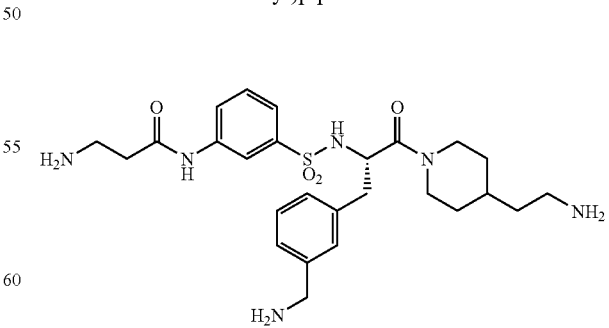

57 mg (0.3 mmol) Boc-βAla-OH were dissolved in 2 ml DMF and treated with 33 µl NMM and 39 µl CKIBE at −15° C. The reaction solution is stirred for 10 min at −15° C. and then treated with 200 mg (0.303 mmol) 3-NH$_2$-phenyl sulfonyl Phe(3-Boc-Ame)-4-(2-Boc-amidoethyl)piperidide. The reaction solution is stirred for 1 h at −15° C. and overnight at RT. The SV is removed u.V., the remainder is precipitated in EE and washed 3 times with 5% KHSO4 solution, once with saturated NaCl solution, 3 times with saturated NaHCO₃-solution and 3 times with saturated NaCl solution. The SV is dried with $Na_2SO_4$ and removed through a vacuum. The residual remainder is treated with 1.5 ml TFA, shaken for 1.5 h, and the product is purified through preparative HPLC as well as lyophilized.

Yield: 90 g white lyophilized powder, MS ber.: 530.27; gef.: 531.4 [M+H]⁺,

HPLC: 18.89% B

Further inhibitors with central 3-aminomethyl phenylalanine were synthesized following the standard methods described above (table 3).

TABLE 3

| Example/Nr. | Structure | HPLC (% B) | MS calculated (M + H)⁺ found |
|---|---|---|---|
| 35 | 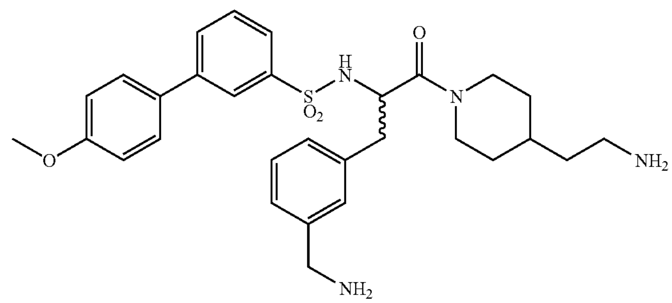 [SMILES: COc1ccc(-c2cccc(S(=O)(=O)NC(Cc3cccc(CN)c3)C(=O)N3CCC(CCN)CC3)c2)cc1] | 33.67 | 550.26 551.2 |
| 36 | 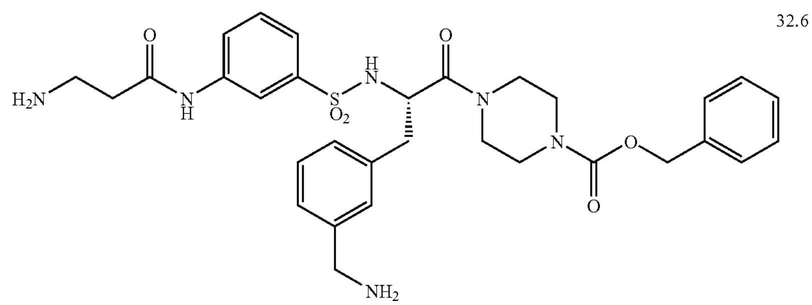 | 32.6 | 622.26 623.3 |

Further Examples

| Example/Nr. | Structure | HPLC (% B) | MS calculated (M + H)⁺ found |
|---|---|---|---|
| 37 | 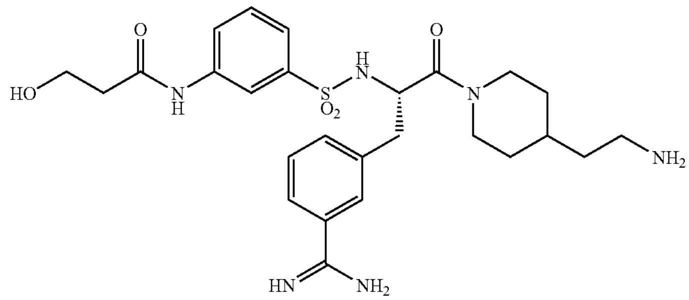 [SMILES: N=C(N)c1cccc(C[C@H](NS(=O)(=O)c2cccc(NC(=O)CCO)c2)C(=O)N2CCC(CCN)CC2)c1] | 20.38 | 544.25 545.3 |

-continued

| Example/Nr. | Structure | HPLC (% B) | MS calculated (M + H)+ found |
|---|---|---|---|
| 38 | 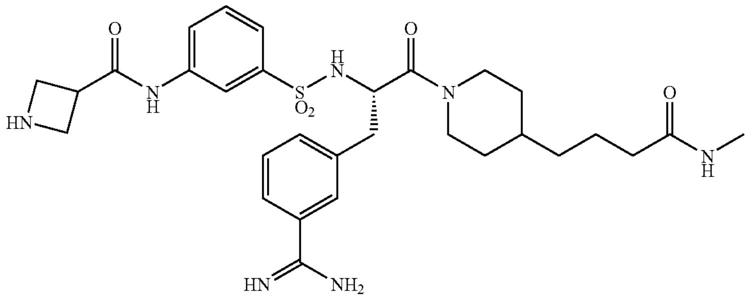 [SMILES: CNC(=O)CCCC1CCN(C(=O)[C@H](Cc2cccc(C(=N)N)c2)NS(=O)(=O)c2cccc(NC(=O)C3CNC3)c2)CC1] | 24.58 | 611.29 612.3 |
| 39 | 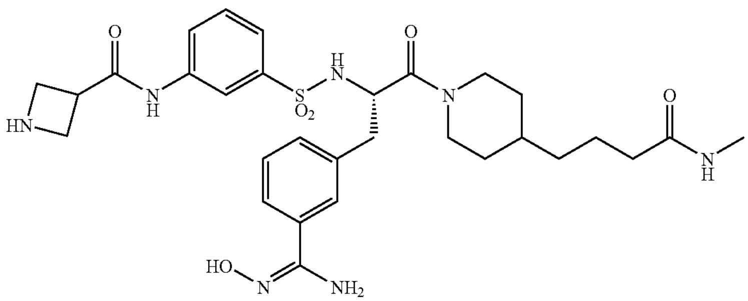 [SMILES: CNC(=O)CCCC1CCN(C(=O)[C@H](Cc2cccc(/C(N)=N\O)c2)NS(=O)(=O)c2cccc(NC(=O)C3CNC3)c2)CC1] | 23.83 | 627.28 628.3 |
| 40 | 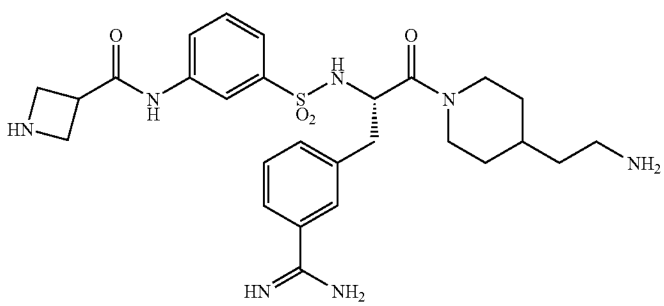 [SMILES: N=C(N)c1cccc(C[C@H](NS(=O)(=O)c2cccc(NC(=O)C3CNC3)c2)C(=O)N2CCC(CCN)CC2)c1] | 18.13 | 555.26 556.3 |
| 41 | 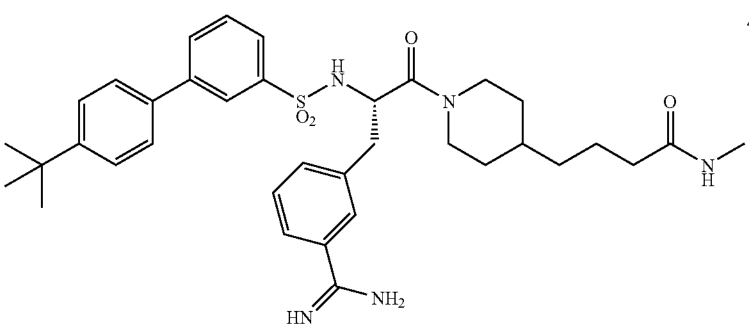 | 49.09 | 645.33 646.6 |

-continued
| Example/Nr. | Structure | HPLC (% B) | MS calculated (M + H)+ found |
|---|---|---|---|
| 42 | 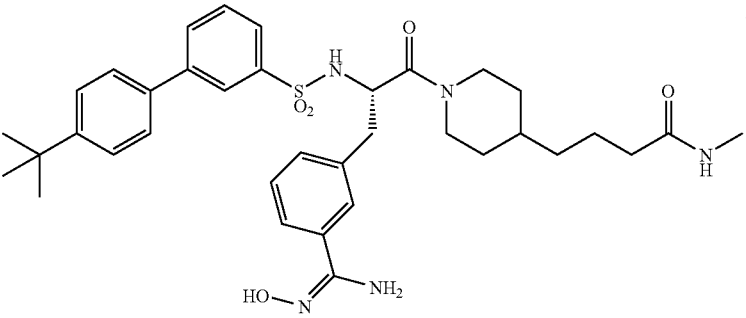 [SMILES: CNC(=O)CCCC1CCN(C(=O)[C@H](Cc2cccc(/C(N)=N\O)c2)NS(=O)(=O)c2cccc(-c3ccc(C(C)(C)C)cc3)c2)CC1] | 26.37 | 609.31 610.3 |
| 43 | 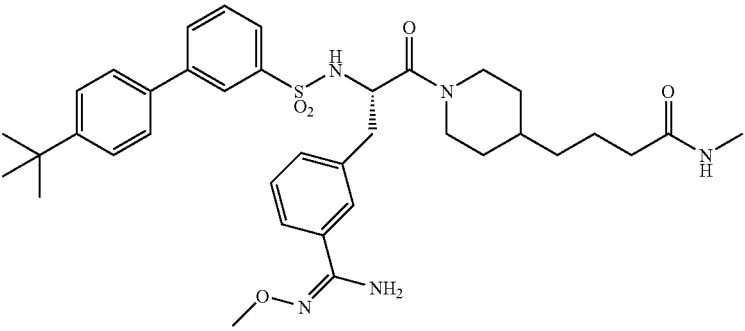 [SMILES: CNC(=O)CCCC1CCN(C(=O)[C@H](Cc2cccc(/C(N)=N\OC)c2)NS(=O)(=O)c2cccc(-c3ccc(C(C)(C)C)cc3)c2)CC1] | — | 675.3 — |
| 44 | 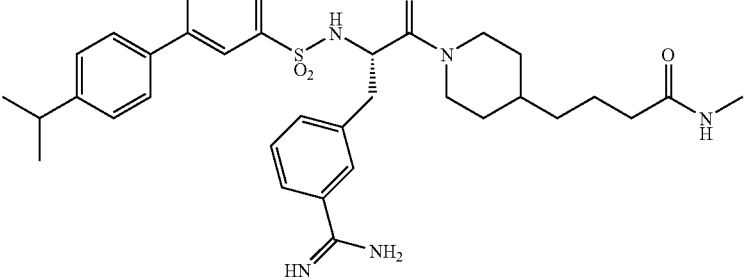 | 47.3 | 631.32 632.3 |
| 45 | 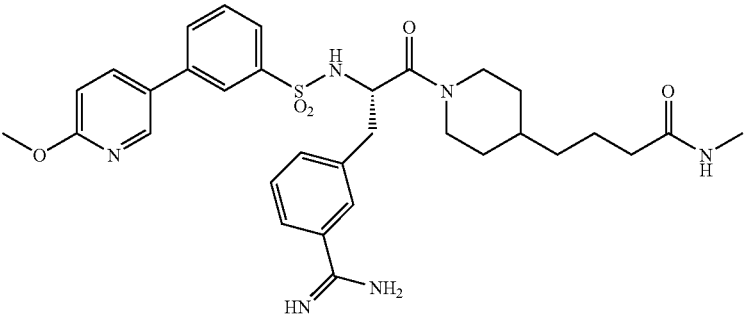 | — | 620.28 — |

| Example/Nr. | Structure | HPLC (% B) | MS calculated (M + H)+ found |
|---|---|---|---|
| 46 | 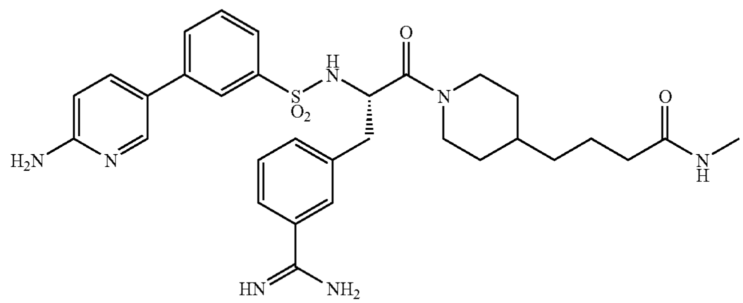 [SMILES: CNC(=O)CCCC1CCN(C(=O)[C@H](Cc2cccc(C(=N)N)c2)NS(=O)(=O)c2cccc(-c3ccc(N)nc3)c2)CC1] | 26.3 | 605.28 606.3 |
| 47 | 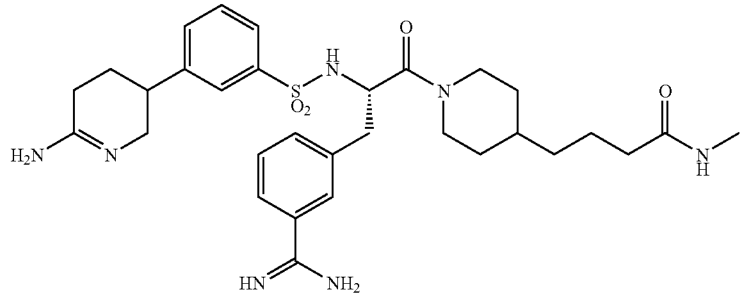 [SMILES: CNC(=O)CCCC1CCN(C(=O)[C@H](Cc2cccc(C(=N)N)c2)NS(=O)(=O)c2cccc(C3CCC(N)=NC3)c2)CC1] | 26.37 | 609.31 610.3 |
| 48 | 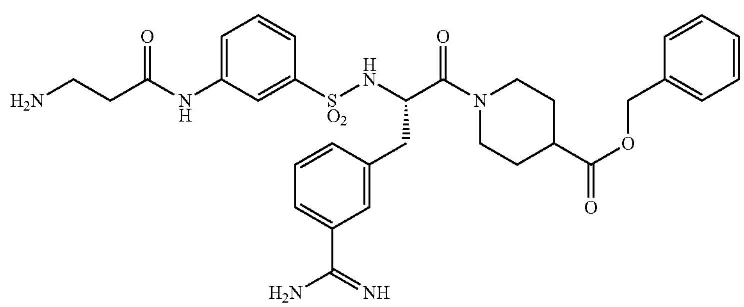 [SMILES: N=C(N)c1cccc(C[C@H](NS(=O)(=O)c2cccc(NC(=O)CCN)c2)C(=O)N2CCC(C(=O)OCc3ccccc3)CC2)c1] | 34.59 | 634.26 635.32 |
PEG-Coupled Inhibitors
Example 49
CH$_3$-PEG$_{1000}$-CH$_2$—CH$_2$—CO-Dap-3-NH-phenyl sulfonyl-Phe(3-Am)-4-(2-amino ethyl)-piperidide×2 acetate
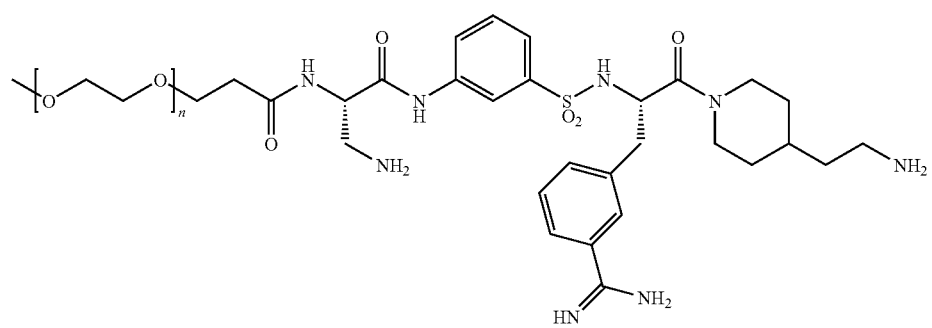

20 mg (20.3 µmol) H-Dap(Boc)-3-NH-phenyl sulfonyl-Phe(3-Am)-4-(2-Boc-amidoethyl)piperidide×2 TFA and 7.05 µl DIEA (40.5 mmol) were dissolved in 1 ml DMF and 2 ml ACN and treated with 203 mg (ca. 20 mop mPEG-SPA-10 kDa (Nektar Therapeutics, USA) at room temperature. The reaction solution was stirred overnight and the solvent was removed u.V. The remainder was uncoupled with a little methanol, the intermediate product precipitated with diethyl ether and extracted (HPLC with Jupiter column: 49.85% B). The intermediate product was treated with 3 ml TFA, stirred for 1 h, the SV compressed u.V., the remainder dissolved in a little methanol, precipitated with diethyl ether and the raw product was extracted. The product was purified by means of ion exchange chromatography using Fractogel CE and an ammonium acetate gradient, and lyophilized 3× from water.

Yield: 82 mg white lyophilized powder

MS for example for n=240: ber.: 11217.4; gef.: 11218.6 [M+H]$^+$

HPLC: 44.79% B in Jupiter column

Example 50

H-βAla-3-NH-phenyl sulfonyl-Phe(3-Am)-4-piperidyl-(CH$_2$)$_3$—CONH—(CH$_2$)$_2$-PEG10000-CH$_3$×2 acetate 11.5 mg (13.8 mop Cbz-βAla-3-NH-phenyl sulfonyl-Phe(3-Am)-4-piperidine butyric acid×TFA and 139 mg NH$_2$-PEG$_{10000}$-CH$_3$ (Rapp Polymer, Germany) were dissolved in 3 ml DMF and 1 ml ACN and treated with 8 mg PyBop and 5 µl DIEA at 0° C. The reaction solution is stirred for 15 min at 0° C. and overnight at RT. The SV is removed u.V. and the remainder dissolved (HPLC with Jupiter column: 47.44% B) dissolved in 5 ml 90% acetic acid and hydrogenated overnight with hydrogen and Pd/C as a catalyst. The catalyst is filtered out, the SV compressed u.V., dissolved in a little methanol and precipitated through the addition of diethyl ether. The extracted raw product was purified by means of ion exchange chromatography using Fractogel CE and an ammonium acetate gradient and lyophilized 3× from water.

Yield: 22 mg white lyophilized powder

HPLC: 45.77% B in Jupiter column

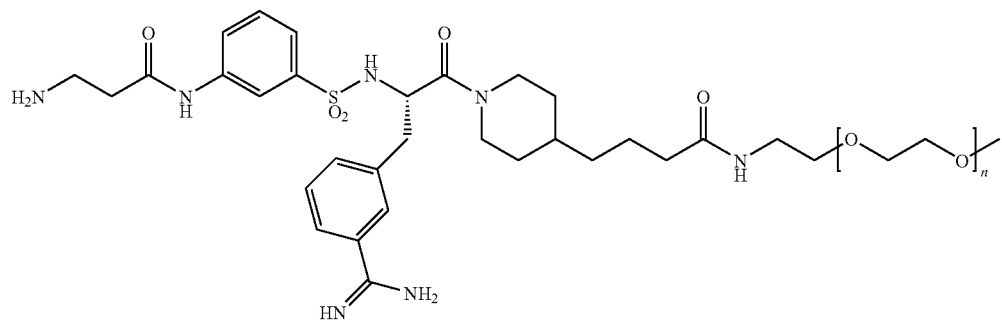

Further PEG-coupled inhibitors were produced by means of standard methods (table 4).

TABLE 4

| Example/ Nr. | Structure | HPLC (% B) |
|---|---|---|
| 51 | 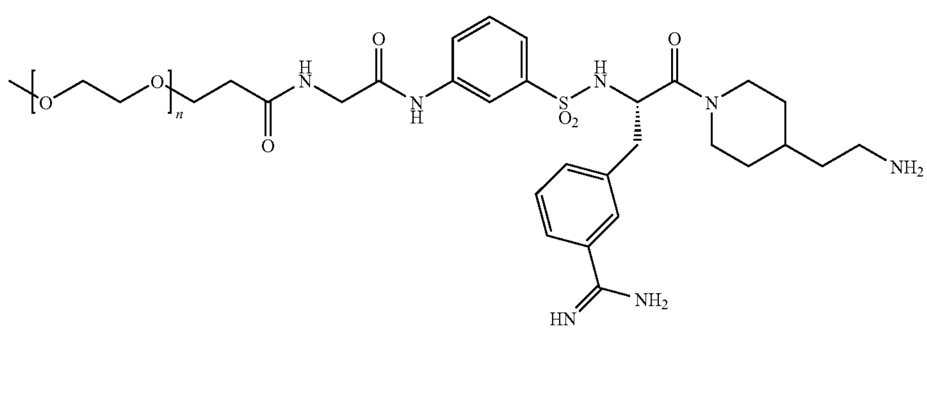 | 45.65 |

TABLE 4-continued

| Example/Nr. | Structure | HPLC (% B) |
|---|---|---|
| 52 | (see structure below) | 44.6 |

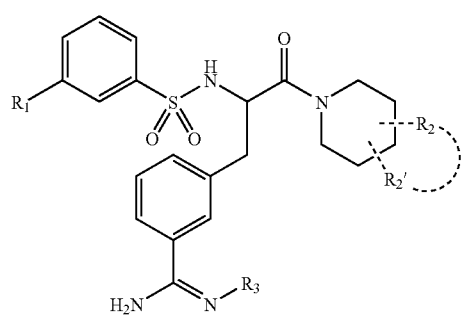

Determination of the Matriptase Inhibition

To determine the inhibition effect, 200 μl Tris buffer (inhibitor contains 0.05 M, 0.154 M NaCl, 5% ethanol, pH 8.0), 25 μl substrate (CH$_3$SO$_2$-D-Cha-Gly-Arg-pNA; 2 and 1 mM) and 50 μl matriptase (0.5 μg/ml) were incubated at 25° C. After 3 min the reaction was halted through the addition of 25 μl acetic acid (50%) and the Absorption determined at 405 nm by means of a Microplate Reader (Multiscan Ascent from the company Thermo Electron Corporation). The K$_i$ values were calculated according to Dixon (Biochem. J. 55, 170-171, 1953) through linear regression by means of a computer program. The K$_i$-values are the means of at least two determinations.

Ki value for the inhibition of matriptase in nM (n.d.=not determined)

| Example/Nr. | Ki (nM) |
|---|---|
| Inhibitor 1: | 5.4 |
| Inhibitor 2: | 100 |
| Inhibitor 3: | 6.0 |
| Inhibitor 4: | 5.4 |
| Inhibitor 5: | 2.5 |
| Inhibitor 6: | 12 |
| Inhibitor 7: | 26 |
| Inhibitor 8: | 91 |
| Inhibitor 9: | 29 |
| Inhibitor 10: | 60 |
| Inhibitor 11: | 47 |
| Inhibitor 12: | 28 |
| Inhibitor 13: | 13 |
| Inhibitor 14: | 4.2 |
| Inhibitor 15: | 0.069 |
| Inhibitor 16: | 0.74 |
| Inhibitor 17: | 6.3 |
| Inhibitor 18: | 8.1 |
| Inhibitor 19: | 24.5 |
| Inhibitor 20: | 6.1 |
| Inhibitor 21: | 11.8 |
| Inhibitor 22: | 255 |
| Inhibitor 23: | 12.1 |
| Inhibitor 24: | 30.5 |
| Inhibitor 25: | 65 |
| Inhibitor 26: | 6.1 |
| Inhibitor 27: | 36 |
| Inhibitor 28: | 32 |
| Inhibitor 29: | 98 |
| Inhibitor 30: | 31 |
| Inhibitor 31: | 24 |
| Inhibitor 32: | n.d. (Pro-drug) |
| Inhibitor 33: | 24000 (Pro-drug) |
| Inhibitor 34: | 56 |
| Inhibitor 35: | 145 |
| Inhibitor 36 | 44.5 |
| Inhibitor 37 | 117 |
| Inhibitor 38 | 16 |
| Inhibitor 39 | n.d. (Pro-drug) |
| Inhibitor 40 | 1.7 |
| Inhibitor 41 | 87 |
| Inhibitor 42 | n.b (pro-drug) |
| Inhibitor 43 | n.b (pro-drug) |
| Inhibitor 44 | 23.5 |
| Inhibitor 45 | n.d. |
| Inhibitor 46 | 11 |
| Inhibitor 47 | 0.49 |
| Inhibitor 48 | 0.7 |
| Inhibitor 49 | 21.8 |
| Inhibitor 50 | 54 |
| Inhibitor 51 | 130 |
| Inhibitor 52 | 246 |

The invention claimed is:

1. A compound according to the formula (I)

(I)

or a salt thereof, wherein
R$_1$ is a singly or multiply substituted ring structure selected from:
(i) an aryl residue, which may be partially or wholly hydrogenated,
(ii) a heteroaryl residue, which may be partially or wholly hydrogenated,
(iii) a non-hydrogenated aryl residue,
(iv) a non-hydrogenated heteroaryl residue,
(v) a heteroaryl residue with one or two nitrogen atoms,
(vi) a phenyl residue,
(vii) a pyridyl residue, (viii) a pyrimidine residue,
(ix) an indole residue,
(x) a tetrahydropyridyl residue,
(xi) a piperidinon residue, or
(xii) a pyridazinone residue; and $R_2$ and $R_2'$ are each independently:
(i) a ramified or straight chain alkyl residue having 1-6 carbon atoms, wherein one or more methylene groups may be replaced by oxygen or nitrogen,
(ii) a ramified or straight chain amino alkyl residue having 1-6 carbon atoms,
(iii) a ramified or straight chain guanidine alkyl residue having 1-6 carbon atoms,
(iv) —$(CH_2)_m$—$C(=O)$—$NHR_4$ where m equals a whole number from 0 to 4 and $R_4$ is a hydrogen or a —$(CH_2)_k$—$CH_3$ residue where k equals a whole number from 0 to 3, or
(v) $R_2$ and $R_2'$ together form a ring structure with the piperidide selected from the group consisting of:

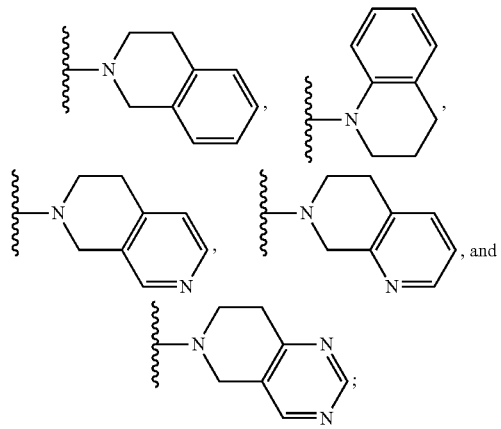

or
$R_1$ is:
(i) a ramified or straight chain hydroxy alkyl residue having 1 to 6 carbon atoms,
(ii) a straight chain aminoalkyl residue,
(iii) a 3-azetidin-$C(=O)$—NH-residue, or
(iv) an unramified n-amino butyl residue; and $R_2$ and $R_2'$ are each independently:
(i) a ramified or straight chain aminoalkyl residue having 1-6 carbon atoms,
(ii) a ramified or straight chain guanidino alkyl residue having 1-6 carbon atoms,
(iii) a straight chain amino ethyl residue, or
(iv) $R_2$ is —$(CH_2)_m$—$C(=O)$—$NHR_4$ where m equals a whole number from 0 to 4, and $R_4$ is a hydrogen or a —$(CH_2)_k$—$CH_3$ residue where k equals a whole number from 0 to 3;

or
$R_1$ is:
(i) a $H_2N$—$(CH_2)_n$—$C(=O)$—NH-residue where n equals a whole number from 1 to 4,
(ii) a HO—$(CH_2)_n$—$C(=O)$—NH-residue where n equals a whole number from 1 to 4, or
(iii) a 3-azetidin-$C(=O)$—NH-residue; and $R_2$ and $R_2'$ are:
(i) each independently a non-basic residue,
(ii) $R_2$ is —$(CH_2)_m$—$C(=O)$—$NHR_4$ where m equals a whole number from 0 to 4, and $R_4$ is a hydrogen or a —$(CH_2)_k$—$CH_3$ residue where k equals a whole number from 0 to 3, and $R_2'$ is a non-basic residue,
(iii) $R_2$ is —$(CH_2)_o$—$C(=O)$—$OR_5$ where o is a whole number from 1 to 6 and $R_5$ is a hydrogen or a ramified or straight chain alkyl group with 1 to 4 carbon atoms, and $R_2'$ is a non-basic residue, or
(iv) $R_2$ and $R_2'$ together form a ring structure with the piperidide selected from the group consisting of:

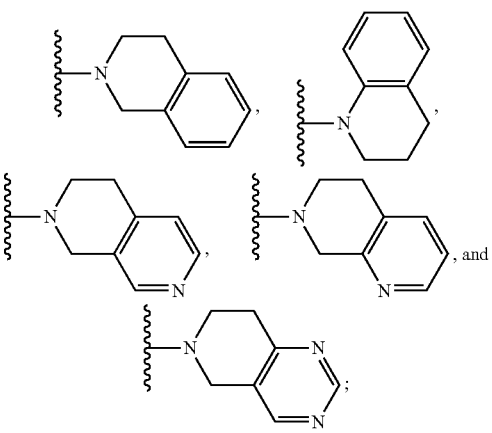

and
$R_3$ is selected from the group consisting of a hydrogen, a hydroxyl group, an alkoxy group, an acetyloxy group and an alkyloxycarbonyl group, whereby the alkyl residue contains 1-6 carbon atoms.

2. The compound according to the claim 1, wherein
$R_2'$ is not present;
$R_1$ is selected from the group consisting of a singly or multiply substituted phenyl residue, pyridyl residue, pyrimidine residue, indole residue, tetrahydropyridyl residue, piperidinon residue and pyridazinone residue; and
$R_2$ is:
(i) a straight chain aminoalkyl residue having 1-6 carbon atoms, or
(ii) —$(CH_2)_m$—$C(=O)$—$NHR_4$ where m equals a whole number from 0 to 4, and $R_4$ is a hydrogen or a —$(CH_2)_k$—$CH_3$ residue where k equals a whole number from 0 to 3;

or
$R_1$ and $R_2$ are:
(i) each independently a straight chain aminoalkyl residue having 1 to 6 carbon atoms, or
(ii) $R_1$ is an unramified n-amino butyl residue and $R_2$ is a straight chain aminoalkyl residue having 1 to 6 carbon atoms;

or
$R_1$ is a $H_2N$—$(CH_2)_n$—$C(=O)$—NH-residue where n equals a whole number from 1 to 4; and
$R_2$ is:
(i) —$(CH_2)_m$—$C(=O)$—$NHR_4$ where m equals a whole number from 0 to 4, and $R_4$ is a hydrogen or a —$(CH_2)_k$—$CH_3$ residue where k equals a whole number from 0 to 3, or
(ii) —$(CH_2)_o$—$C(=O)$—$OR_5$ where o is a whole number from 1 to 6, and $R_5$ is a hydrogen or a straight chain alkyl group with 1 to 4 carbon atoms;

and

R₃ is selected from the group consisting of a hydrogen, a hydroxyl group, an alkoxy group, an acetyloxy group and an alkyloxycarbonyl group, whereby the alkyl residue contains 1-6 carbon atoms.

3. The compound according to claim 1, wherein R₂ is in the meta or para position.

4. The compound according to claim 1, wherein R₂ is in the para position and R₂' in the ortho or meta position.

5. The compound according to claim 1, wherein R₁ is a ring structure substituted in the meta position, the para position, or both the meta and para positions.

6. The compound according to claim 5, wherein each substitution of R₁ is independently selected from the group consisting of: R₆—O—, where R₆ is a ramified or straight chain alkyl residue with 1 to 6 carbon atoms; $(CH_3)-(CH_2)_p-$, where p equals a whole number from 0 to 6; a halogen; chlorine; and an amino group.

7. The compound according to claim 1, wherein R₁ is a phenyl residue substituted in the meta position, the para position, or both the meta and para positions, and wherein each substitution is independently selected from the group consisting of: R₆—O—, where R₆ is a ramified or straight chain alkyl residue with 1 to 6 carbon atoms; $(CH_3)-(CH_2)_p-$ where p equals a whole number from 0 to 6; a halogen; and chlorine.

8. The compound according to claim 1, wherein R₁ is a pyridyl residue, a pyrimidine residue or a tetrahydropyridyl residue, wherein the residue is substituted in the meta position, the para position, or both the meta and para positions, and wherein each substitution is independently selected from the following residues: $(CH_3)-(CH_2)_p-$ where p equals a whole number from 0 to 6; and an amino group.

9. The compound according to claim 8, wherein R₁ is a pyridyl residue substituted with an amino group or a tetrahydropyridyl residue substituted with an amino group.

10. The compound according to claim 8, wherein R₁ is a pyrimidine residue substituted with a $(CH_3)-(CH_2)_p$-group where p equals a whole number from 0 to 6.

11. The compound according to claim 1, wherein a polyethyleneglycol chain is covalently coupled to the compound by a linker.

12. The compound according to claim 1, wherein amino acids present as central structure motifs in the formulas (I), (II) and (III) are in the L-configuration.

13. A compound selected from the group consisting of:
3-(3,4-dimethoxyphenyl)phenyl sulfonyl-L-phenylalanine(3-amidino)-4-(2-amino ethyl)piperidide,
3-(phenyl)phenyl sulfonyl-L-phenylalanine(3-amidino)-4-(2-amino ethyl)piperidide,
3-(4-methoxyphenyl)phenyl sulfonyl-L-phenylalanine(3-amidino)-4-(2amino ehtyl)piperidide,
3-(4-ethoxyphenyl)phenyl sulfonyl-L-phenylalanine(3-amidino)-4-(2amino ehtyl)piperidide,
3-(4-ethylphenyl)phenyl sulfonyl-L-phenylalanine(3-amidino)-4-(2-amino ethyl)piperidide,
3-(4-isopropoxyphenyl)phenyl sulfonyl-L-phenylalanine(3-amidino)-4-(2-amino ethyl)piperidide,
3-(4-chlorphenyl)phenyl sulfonyl-L-phenylalanine(3-amidino)-4-(2-Amino ethyl)piperidide,
3-(3-chlorphenyl)phenyl sulfonyl-L-phenylalanine(3-amidino)-4-(2-Amino ethyl)piperidide,
3-(2-chlorphenyl)phenyl sulfonyl-L-phenylalanine(3-amidino)-4-(2-Amino ethyl)piperidide,
3-(4-pyridyl)phenyl sulfonyl-L-phenylalanine(3-amidino)-4-(2-amino ethyl)piperidide,
3-(3-pyridyl)phenyl sulfonyl-L-phenylalanine(3-amidino)-4-(2-amino ethyl)piperidide,
3-(2-methyl-4-pyrimidinyl)phenyl sulfonyl-L-phenylalanine(3-amidino)-4-(2-amino ethyl)piperidide,
3-(5-indolyl)phenyl sulfonyl-L-phenylalanine(3-amidino)-4-(2-amino ethyl)piperidide,
3-(4-amino-3-pyridyl)phenyl sulfonyl-L-phenylalanine(3-amidino)-4-(2-amino ethyl)piperidide,
3-(4-amino-3-tetrahydropyridyl)phenyl sulfonyl-L-phenylalanine(3-amidino)-4-(2-amino ethyl)piperidide,
3-(1-amino butyl)-phenyl sulfonyl-L-phenylalanine(3-amidino)-4-(2-amino ethyl)piperidide,
3-(H-β-alanyl-NH)phenyl sulfonyl-L-phenylalanine(3-amidino)-4-(methylamido buteryl)piperidide,
3-(4-ethoxyphenyl)phenyl sulfonyl-L-phenylalanine(3-amidino)-4-(methylamido buteryl)piperidide,
3-(4-ethylphenyl)phenyl sulfonyl-L-phenylalanine(3-amidino)-4-(methylamido buteryl)piperidide,
3-(H-β-alanyl-NH)phenyl sulfonyl-L-phenylalanine(3-amidino)-4-piperidinbuteryl-O-methylat,
3-(H-β-alanyl-NH)phenyl sulfonyl-L-phenylalanine(3-amidino)-4-(amido buteryl)piperidide,
3-(H-β-alanyl-NH)phenyl sulfonyl-L-phenylalanine(3-amidino)-4-(buteryl)piperidide,
3-(H-β-alanyl-NH)phenyl sulfonyl-L-phenylalanine(3-amidino)-isonipecotylamide,
3-(H-β-alanyl-NH)phenyl sulfonyl-L-phenylalanine(3-amidino)-nipecotyl amide,
3-(H-β-alanyl-NH)phenyl sulfonyl-L-phenylalanine(3-amidino)-4-(ethyloxycarbonyl) piperazid,
3-(H-β-alanyl-NH)phenyl sulfonyl-L-phenylalanine(3-amidino)-4-benzyloxycarbonyl) piperazid,
3-(H-β-alanyl-NH)phenyl sulfonyl-L-phenylalanine(3-amidino)-piperazid,
3-(H-β-alanyl-NH)phenyl sulfonyl-L-phenylalanine(3-amidino)-piperidide,
3-(pyridazinone)phenyl sulfonyl-L-phenylalanine(3-amidino)-4-(methylamido buteryl) piperidide,
3-(piperidinon)phenyl sulfonyl-L-phenylalanine(3-amidino)-4-(methylamido buteryl) piperidide,
3-(piperazinone)phenyl sulfonyl-L-phenylalanine(3-amidino)-4-(methylamido buteryl) piperidide,
3-(4-ethoxyphenyl)phenyl sulfonyl-L-phenylalanine(3-hydroxyamidino)-piperidine buteryl-N-methylamide,
3-(4-ethylphenyl)phenyl sulfonyl-L-phenylalanine(3-hydroxyamidino)-piperidine buteryl-N-methylamide,
3-(H-βalanine-NH)phenyl sulfonyl-L-phenylalanine(3-aminomethyl)-4-(2-amino ethyl) piperidide,
3-(4-methoxyphenyl)phenyl sulfonyl-L-phenylalanine(3-aminomethyl)-4-(2-amino ethyl)piperidide,
3-(H-β-alanyl-NH)phenyl sulfonyl-L-phenylalanine(3-aminomethyl)-4-(benzyloxycarbonyl)piperazid,
3-(1-hydroxybutyl)-phenyl sulfonyl-L-phenylalanine(3-amidino)-4-(2-amino ethyl) piperidide,
3-(3-azetidin-CONH)-phenyl sulfonyl-L-phenylalanine(3-amidino)-4-(methylamido buteryl)piperidide,
3-(3-azetidin-CONH)-phenyl sulfonyl-L-phenylalanine(3-hydroxyamidino)-4-(methylamido buteryl)piperidide,
3-(3-azetidin-CONH)-phenyl sulfonyl-L-phenylalanine(3-amidino)-4-(2-amino ethyl)piperidide,
3-(4-tert-butylphenyl)phenyl sulfonyl-L-phenylalanine(3-amidino)-4-(methylamido buteryl)piperidide,
3-(4-tert-butylphenyl)phenyl sulfonyl-L-phenylalanine(3-hydroxyamidino)-4-(methylamido buteryl)piperidide,
3-(4-tert-butylphenyl)phenyl sulfonyl-L-phenylalanine(3-methoxyamidino)-4-(methylamido buteryl)piperidide,
3-(4-isopropylphenyl)phenyl sulfonyl-L-phenylalanine(3-amidino)-4-(methylamido buteryl)piperidide, 3-(4-methoxy-3-pyridyl)phenyl sulfonyl-L-phenylalanine (3-amidino)-4-(methylamido buteryl)piperidide, 3-(4-amino-3-pyridyl)phenyl sulfonyl-L-phenylalanine (3-amidino)-4-(methylamido buteryl)piperidide, 3-(4-amino-3-tetrahydropyridyl)phenyl sulfonyl-L-phenylalanine(3-amidino)-4-(methylamido buteryl)piperidide, 3-(Nα-($CH_3$-$PEG_{10000}$-$CH_2$-$CH_2$-CO)-α,β-diaminopropionyl-NH)phenyl sulfonyl-L-phenylalanine (3-amidino)-4-(2-amino ethyl)-piperidide, 3-(H-β-alanyl-NH)phenyl sulfonyl-L-phenylalanine(3-amidino)-4-($CH_3$-$PEG_{10000\text{-}CH2}$-$CH_2$-amido buteryl) piperidide, 3-($CH_3$-$PEG_{10000}$-$CH_2$-$CH_2$-CO)-β-Ala-NH)phenyl sulfonyl-L-phenylalanine(3-amidino)-4-(2-amino ethyl)-piperidide, 3-(H-β-alanyl-NH)phenyl sulfonyl-L-phenylalanine(3-amidino)-4-($CH_3$-$PEG_{10000}$-$CH_2$-$CH_2$-NH-Suc)piperazid, and 3-(H-β-alanyl-NH)phenyl sulfonyl-L-phenylalanine(3-amidino)-nipecotyl-benzyl ester.

14. A pharmaceutical composition comprising a compound of claim 1.

15. A method for inhibiting or treating tumor metastasis in a subject, comprising administering a pharmaceutical composition of claim 14 to a subject having a tumor, thereby inhibiting or treating tumor metastasis.

16. A method for inhibiting of matriptase in a subject, comprising administering a pharmaceutical composition of claim 14 to a subject, thereby inhibiting matriptase.

17. An in vitro method for inhibiting matriptase, comprising contacting a cell expressing matriptase with a compound of claim 1, thereby inhibiting matriptase.

18. A pharmaceutical composition comprising a compound of claim 13.

19. A method for treating tumor metastasis in a subject, comprising administering a pharmaceutical composition of claim 18 to a subject having a tumor, thereby treating tumor metastasis.

20. A method for inhibiting matriptase in a subject, comprising administering a pharmaceutical composition of claim 18 to a subject, thereby inhibiting matriptase.

21. An in vitro method for inhibiting matriptase, comprising contacting a cell expressing matriptase with a compound of claim 18, thereby inhibiting matriptase.

* * * * *

UNITED STATES PATENT AND TRADEMARK OFFICE
CERTIFICATE OF CORRECTION

PATENT NO. : 8,569,313 B2  Page 1 of 1
APPLICATION NO. : 12/529767
DATED : October 29, 2013
INVENTOR(S) : Steinmetzer et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 922 days.

Signed and Sealed this
Twenty-second Day of September, 2015

Michelle K. Lee
*Director of the United States Patent and Trademark Office*